(12) United States Patent
Lindsey et al.

(10) Patent No.: US 8,188,298 B2
(45) Date of Patent: May 29, 2012

(54) SYNTHETIC ROUTE TO ABCD-PORPHYRINS

(75) Inventors: Jonathan S. Lindsey, Raleigh, NC (US);
Dilek Dogutan Kiper, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 13/170,492

(22) Filed: Jun. 28, 2011

(65) Prior Publication Data

US 2011/0306774 A1   Dec. 15, 2011

Related U.S. Application Data

(62) Division of application No. 12/029,070, filed on Feb. 11, 2008, now Pat. No. 7,994,312.

(60) Provisional application No. 60/889,344, filed on Feb. 12, 2007.

(51) Int. Cl.
*C07F 15/00* (2006.01)
*C07D 403/14* (2006.01)

(52) U.S. Cl. ......................... 548/402; 548/518

(58) Field of Classification Search .................. 548/402, 548/518
See application file for complete search history.

(56) References Cited

U.S. PATENT DOCUMENTS

| 6,559,374 | B2 | 5/2003 | Lindsey et al. |
| 6,765,092 | B2 | 7/2004 | Lindsey et al. |
| 6,849,730 | B2 | 2/2005 | Lindsey et al. |
| 6,946,552 | B2 * | 9/2005 | Lindsey et al. ............... 540/145 |
| 7,153,975 | B2 | 12/2006 | Lindsey et al. |
| 2007/0055060 | A1 | 3/2007 | Lindsey et al. |

FOREIGN PATENT DOCUMENTS

EP   1 734 594 A2   12/2006

OTHER PUBLICATIONS

Strachan J-P et al. Rational synthesis of meso-substituted chlorin building blocks. J. Org. Chem. (2000), vol. 65, pp. 3160-3172.
Rao, P D et al. Rational syntheses of porphyrins bearing up to four different meso substituents. J. Org. Chem. (2000), vol. 65, pp. 7323-7344.
Zaidi S H H et al. Investigation of streamlined syntheses of porphyrins bearing distinct meso substituents. Organic Process Research & Development (2006), vol. 10, pp. 118-134.
International Search Report and Written Opinion, PCT/US08/01774, issued Jun. 13, 2008.
International Preliminary Report on Patentability, PCT/US08/01774, issued Aug. 19, 2009.
Dogutan DK and Lindsey JS. Investigation of the scope of a new route to ABCD-bilanes and ABCD-porphyrins. Journal of Organic Chemistry. 2008; 73(17): 6728-6742.

* cited by examiner

*Primary Examiner* — Joseph Kosack
(74) *Attorney, Agent, or Firm* — Myers Bigel Sibley & Sajovec, P.A.

(57) ABSTRACT

A method of making a metalloporphyrin is carried out by reacting (i) a linear tetrapyrrole, said linear tetrapyrrole having a 19-acyl group and a 1-protecting group, with (ii) a metal salt under basic conditions to produce the metalloporphyrin. Products produced by such methods and intermediates useful for carrying out such methods are also described.

16 Claims, No Drawings

SYNTHETIC ROUTE TO ABCD-PORPHYRINS

RELATED APPLICATIONS

This application is a divisional of and claims priority to U.S. patent application Ser. No. 12/029,070, now allowed now U.S. Pat. No. 7,994,312, and claims the benefit of U.S. Provisional Patent Application Ser. No. 60/889,344, filed Feb. 12, 2007, the disclosure of each of which is incorporated by reference herein in its entirety.

GOVERNMENT FUNDING

This invention was made with government support under grant number GM36238 from the National Institutes of Health. The US Government has certain rights to this invention.

FIELD OF THE INVENTION

The present invention concerns porphyrin compounds and methods and intermediates useful for making the same.

BACKGROUND OF THE INVENTION

Porphyrins bearing four different meso substituents are important building blocks for biomimetic and materials chemistry. The existing method for the synthesis of such ABCD-porphyrins is shown in Scheme 1. The porphyrin-forming reaction entails acid-catalyzed condensation of a dipyrromethane-1,9-dicarbinol (I)+a dipyrromethane (II), which is believed to proceed via a bilane-carbinol (III) and a porphyrinogen (IV) with competing formation of polypyrromethanes (V). Treatment of the reaction mixture with an oxidant gives the porphyrin (VI).[1,26] The current method enables synthesis of ~1 g quantities of variously substituted ABCD-porphyrins with low or no detectable scrambling.

In developing access to ABCD-porphyrins, we have attempted to meet the following criteria: (1) little or no scrambling at any stage of the synthesis, (2) limited reliance on chromatography, (3) scalable syntheses affording at least 1 g of porphyrin, (4) straightforward implementation in a reasonable period (e.g., <1 week), (5) broad scope in terms of ABCD substituents, and (6) good yield. These criteria have been met in part. The procedures for forming the dipyrromethane and elaborating the dipyrromethane to give the dipyrromethane-1,9-dicarbinol are reasonably well developed and meet all six of the objectives outlined above. However, the final porphyrin-forming step still presents a number of limitations.

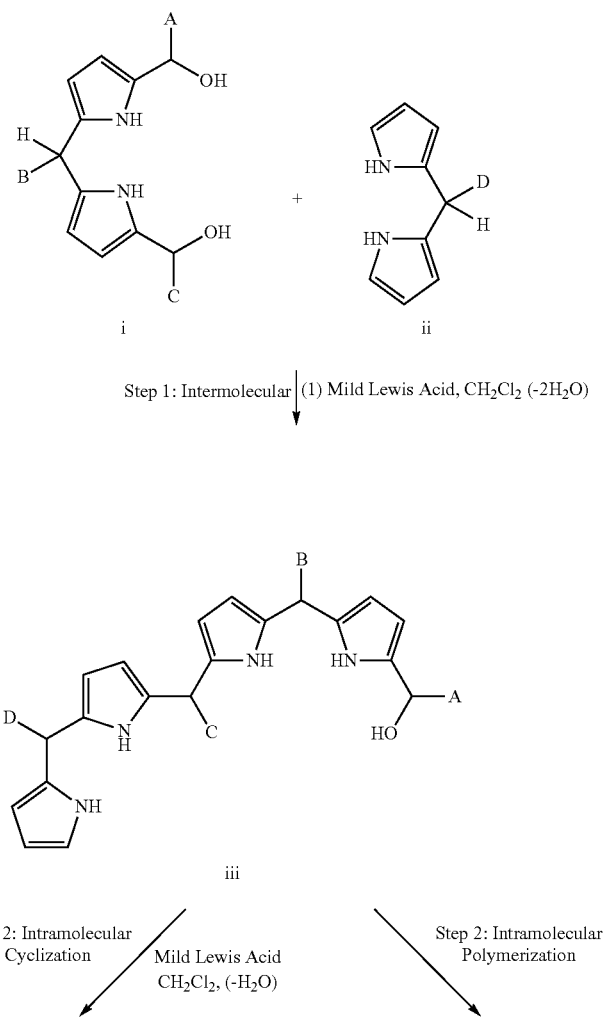

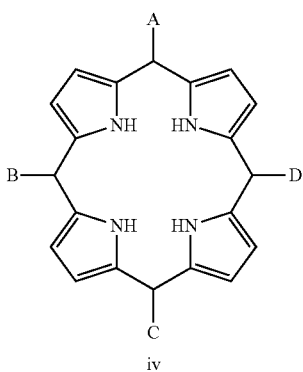

iv

|Oxidation (-6 e⁻, -6 H⁺)

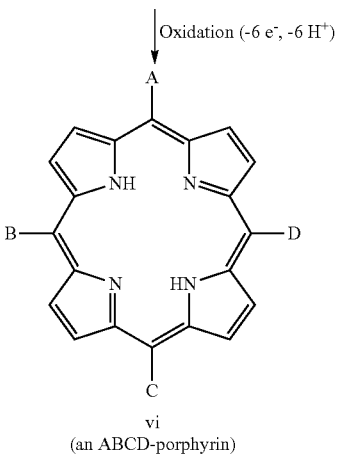

vi
(an ABCD-porphyrin)

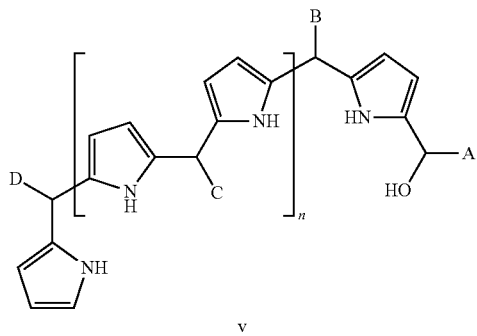

v

The drawbacks of the porphyrin-forming procedure include: (1) low concentration (2.5 or 25 mM), (2) low yield (15-22%), and (3) requisite use of column chromatography to purify the porphyrin. Such drawbacks need to be overcome to facilitate large-scale syntheses. In this regard, a lengthy series of studies was carried out recently to identify improved conditions for the acid-catalyzed condensation of the dipyrromethane-1,9-dicarbinol (I)+a dipyrromethane (II).[1] Although acid catalysis conditions were identified for carrying out the reaction at 25 mM, the highest yield is typically obtained at 2.5 mM reactants. Higher concentrations tend to give larger amounts of polymer owing to the well-known concentration dependence of the competition between cyclization and polymerization (III→IV or V). Moreover, the use of higher concentrations typically requires an increased concentration of acid, whereupon the risk of acid-induced scrambling also is increased. The difficulty in identifying further improvements to the conditions for the 2+2 condensation has made the development of new routes for constructing the porphyrin macrocycle difficult.

SUMMARY OF THE INVENTION

A first aspect of the invention is a method of making a metalloporphyrin, comprising: reacting (i) a linear tetrapyrrole, said linear tetrapyrrole having a 19-acyl group and a 1-protecting group, with (ii) a metal salt under basic conditions to produce said metalloporphyrin. The reacting step may be carried out under any suitable conditions, e.g., in an organic solvent, aqueous solvent, or mixture thereof, or solventless or "neat."

A second aspect of the invention linear tetrapyrrole having a 19-acyl group and a 1-protecting group, wherein said protecting group is selected from the group consisting of halo, thio, acetate, sulfonate, and triflate.

A further aspect of the invention is a complex of (i) a metal ion; (ii) a linear tetrapyrrole, and (iii) optionally at least one counterion; wherein said linear tetrapyrrole has a 19-acyl group substituted thereon, and wherein said linear tetrapyrrole is at least partially unsaturated. The linear tetrapyrrole can be selected from the group consisting of bilins (or "bilatrienes"), bilenes, and biladienes (these terms including metal complexes such as boron complexes thereof). The metal can be magnesium, zinc, copper, palladium, nickel, or indium.

A further aspect of the invention is a complex of the formula $DMR^1R^2$, wherein: D is a linear tetrapyrrole having a 19-acyl group substituted thereon, M is boron, and $R^1$ and $R^2$ are each independently selected from the group consisting of alkyl, alkenyl, alkynyl, and aryl, each of which can be unsubstituted or substituted one or more times with a substituent selected from the group consisting of alkyl, alkenyl, alkynyl, aryl, alkoxy, alkylcarbonyl, alkylcarbonyloxy, alkylsulfinyl, alkylsulfonyl, alkylthio, halo, cyano, nitro, sulfo, oxo, formyl, azido, and carbamoyl. In some embodiments the complex is in solid form.

The foregoing and other objects and aspects of the invention are explained in greater detail in the specification set forth below. The disclosures of all United States patent references cited herein are to be incorporated by reference herein in their entirety.

DETAILED DESCRIPTION OF THE PREFERRED EMBODIMENTS

A. Definitions

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Hydroxyl" as used herein refers to an —OH group.

"Nitro" as used herein refers to an —$NO_2$ group.

"Alkyl" as used herein alone or as part of another group, refers to a straight or branched chain hydrocarbon containing from 1 or 2 to 10, 20 or 50 carbon atoms (e.g., C1 to C4 alkyl; C4 to C10 alkyl; C11 to C50 alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl, in some embodiments preferred, and refers to a straight or branched chain hydrocarbon group containing from 1 to 4 carbon atoms. Representative examples of loweralkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkylene" as used herein refers to a difunctional linear, branched or cyclic alkyl group, which may be substituted or unsubstituted, and where "alkyl" is as defined above.

"Alkenyl" as used herein alone or as part of another group, refers to a straight or branched chain hydrocarbon containing from 1 or 2 to 10, 20 or 50 carbon atoms (e.g., C1 to C4 alkenyl; C4 to C10 alkenyl; C11 to C50 alkenyl) (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadienyl, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkenylene" as used herein refers to a difunctional linear, branched or cyclic alkyl group, which may be substituted or unsubstituted, and where "alkenyl" is as defined above.

"Alkynyl" as used herein alone or as part of another group, refers to a straight or branched chain hydrocarbon containing from 1 or 20 to 10, 20 or 50 carbon atoms (e.g., C1 to C4 alkynyl; C4 to C10 alkynyl; C11 to C50 alkynyl) (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Alkynylene" as used herein refers to a difunctional linear, branched or cyclic alkynyl group, which may be substituted or unsubstituted, and where "alkynyl" is as defined above.

"Alkylidene chain" as used herein refers to a difunctional linear, branched, and/or cyclic organic group, which may be substituted or unsubstituted, which may be saturated or unsaturated, and which may optionally contain one, two or three heteroatoms selected from the group consisting of N, O, and S. Examples include but are not limited to alkylene, alkenylene, alkynylene, arylene, alkarylene, and aralkylene. See, e.g., U.S. Pat. No. 6,946,533. The alkylidene chain may contain any suitable number of carbon atoms (e.g., a C1 to C4; C4 to C10; C10 to C20; C20 to C50).

"Alkoxy" as used herein alone or as part of another group, refers to an alkyl or loweralkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, or a water soluble group.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited to, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Amide" as used herein alone or as part of another group refers to a —C(O)NR$_a$R$_b$ radical, where R$_a$ and R$_b$ are any suitable substituent such as H, alkyl, cycloalkyl, alkenyl, alkynyl or aryl.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Preferred heterocyclo groups include pyridyl and imidazolyl groups, these terms including the quaternized derivatives thereof, including but not limited to quaternary pyridyl and imidazolyl groups, examples of which include but are not limited to:

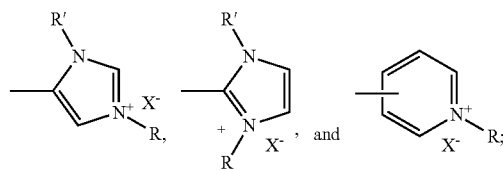

where R and R' are each a suitable substituent as described in connection with "alkyl" above, and particularly alkyl (such as methyl, ethyl or propyl), arylalkyl (such as benzyl), optionally substituted with hydroxy (—OH), phosphonic acid (—PO$_3$H$_2$) or sulfonic acid (—SO$_3$H), and X$^-$ is a counterion.

"Spiroalkyl" as used herein alone or as part of another group, refers to a straight or branched chain hydrocarbon, saturated or unsaturated, containing from 3 to 8 carbon atoms. Representative examples include, but are not limited to, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CHCHCH$_2$—, —CH$_2$CH$_2$CH$_2$CH$_2$CH$_2$CH$_2$—, etc. The term "spiroalkyl" is intended to include both substituted and unsubstituted "spiroalkyl" unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, sulfonamide, urea, alkoxyacylamino, aminoacyloxy, nitro or cyano where m=0, 1 or 2.

"Aldehyde" as used herein refers to a group of the formula:

"Acetal" as used herein refers to a group of the formula:

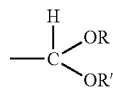

where R and R' are each suitable groups, e.g., groups independently selected from the group consisting of alkyl, aryl, alkylaryl, or where R and R' together form a group —R"— where R" is an alkylene (i.e., cycloalkyl). The acetal is preferably reasonably robust, and hence it is preferred that at least one, or more preferably both, of R and R' is not methyl, and it is particularly preferred that neither R nor R' is H.

"Porphyrinic macrocycle" refers to a porphyrin or porphyrin derivative, and are discussed in greater detail below.

"Macrocyclic ligand" as used herein means a macrocyclic molecule of repeating units of carbon atoms and hetero atoms (e.g., O, S, or NH), separated by the carbon atoms (generally by at least two or three carbon atoms). Macrocyclic ligands exhibit a conformation with a so-called hole capable of trapping ions or molecules, particularly cations, by coordination with the electrons of the hetero atom (e.g., a lone pair of electrons on the oxygen atoms when the hetero atoms are oxygen). In general, the macrocyclic ring contains at least 9, 12 or 14 carbon atoms and hetero atoms (e.g., O, S, NH), each hetero atom in the ring being separated from adjoining hetero atoms in the ring by two or more carbon atoms. The macrocyclic ring may be substituted or unsubstituted, and may be fused to additional rings (e.g., 1 to 4 additional rings such as phenylene, naphthylene, phenanthrylene, and anthrylene rings). The macrocyclic ligand may be in the form of a substituent. See, e.g., U.S. Pat. No. 6,411,164 to Sibert.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates) "Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium as described above) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc. Note that compounds of the present invention can contain both an anionic group as one ionic substituent and a cationic group as another ionic substituent, with the compounds hence being zwitterionic. Note also that the compounds of the invention can contain more than one anionic or more than one cationic group.

"Protecting group" as used herein includes any suitable protecting group; "protected form" refers to a substituent in which an atom such as hydrogen has been removed and replaced with a corresponding protecting group. Protecting groups are known. See generally T. H. Greene and P. G. M. Wuts, *Protective Groups in Organic Synthesis,* 3rd edition, John Wiley & Sons, New York (1999). Examples include but are not limited to: hydroxy protecting groups (for producing the protected form of hydroxy); carboxy protecting groups (for producing the protected form of carboxylic acid); amino-protecting groups (for producing the protected form of amino); sulfhydryl protecting groups (for producing the protected form of sulfhydryl); etc. Particular examples include but are not limited to: benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, acetyl (Ac or —C(O)CH$_3$), benzoyl (Bn or —C(O)C$_6$H$_5$), and trimethylsilyl (TMS or —Si(CH$_3$)$_3$), and the like; formyl, acetyl, benzoyl, pivaloyl, t-butylacetyl, phenylsulfonyl, benzyl, t-butyloxycarbonyl (Boc), and benzyloxycarbonyl (Cbz) and the like; and hemithioacetals such as 1-ethoxyethyl and methoxymethyl, thioesters, or thiocarbonates and the like. See, e.g., U.S. Pat. Nos. 6,953,782; 6,951,946; 6,951,942; and 6,051,724. Particularly preferred are halo, thio (e.g., alkylthio, thiocyanate), acetate, sulfonate, and triflate protecting groups.

"Antibody" as used herein refers generally to immunoglobulins or fragments thereof that specifically bind to antigens to form immune complexes. The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility. Newer techniques for production of monoclonals can also be used, e.g., human monoclonals, interspecies monoclonals, chimeric (e.g., human/mouse) monoclonals, genetically engineered antibodies and the like.

"Coupling agent" as used herein, refers to a reagent capable of coupling a photosensitizer to a targeting agent "Targeting agent" refers to a compound that homes in on or preferentially associates or binds to a particular tissue, receptor, infecting agent or other area of the body of the subject to be treated, such as a target tissue or target composition. Examples of a targeting agent include but are not limited to an antibody, a ligand, one member of a ligand-receptor binding pair, nucleic acids, proteins and peptides, and liposomal suspensions, including tissue-targeted liposomes.

"Specific binding pair" and "ligand-receptor binding pair" as used herein refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (antiligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-alpha and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and their receptors, such as granulocyte-macrophage colony stimulating factor (GMCSF) and GMCSF receptor and macrophage colony stimulating factor (MCSF) and MCSF receptor.

"Linkers", or "linker groups" are aromatic or aliphatic groups (which may be substituted or unsubstituted and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

"Water soluble group" (or "water solubilizing group") as used herein generally includes substituents containing at least one ionic or polar group, coupled to the parent molecule directly or by means of an intervening linker. Examples include but are not limited to groups of the formula:

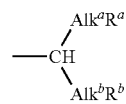

wherein $R^a$ and $R^b$ are each independently an ionic group or polar group, and $Alk^a$ and $Alk^b$ are each independently a C1-C50 alkylidene chain.

"Bronsted acid" as used herein refers to a molecular entity (and corresponding chemical species) that is a proton donor to a base. Any suitable Bronsted acid may be used as a catalyst, with examples including but not limited to: trifluoroacetic acid, trichloroacetic acid, oxalic acid, taurine, malonic acid, formic acid, acetic acid, and $NH_4Cl$.

"Lewis acid" as used herein refers to a molecular entity (and corresponding chemical species) that is an electron-pair acceptor and therefore able to react with a Lewis base to form a Lewis adduct, by sharing the electron pair furnished by the Lewis base. Any suitable Lewis acid may be used as a catalyst, examples including compounds of the general formula $LnX_3$ where Ln is a lanthanide and X is halo such as Cl, Br, I, etc., triflate or OTf, etc., and with examples specific examples including but not limited to: $Yb(OTf)_3$, $InCl_3$, $Sc(OTf)_3$, $MgBr_2$ and $CeCl_3$.

B. Porphyrins and Methods of Making with Linear Tetrapyrroles

A method of making a metalloporphyrin comprises reacting (i) a linear tetrapyrrole with (ii) a metal salt to produce the metalloporphyrin. The linear tetrapyrrole preferably has a 19-acyl group substituted thereon and a 1-protecting group substituted thereon. The method is preferably carried out in a single reaction vessel, or as a "one pot" reaction.

Any suitable linear tetrapyrrole can be used, including bilanes and partially unsaturated (or partially oxidized) linear tetrapyrroles such as bilins ("or bilatrienes"), bilenes, and biladienes. In general: bilanes contain 8 double bonds (e.g., compounds of Formula IIa below), bilenes contain 9 double bonds (e.g., compounds of Formulas IIc and IId below); biladienes contain 10 double bonds (e.g., compounds of Formulas IIe and IIf below); and bilins (or bilatrienes) contain 11 double bonds (e.g., compounds of Formula IIb below), it being understood that additional bonds may be contained on substituents of the linear tetrapyrrole. The linear tetrapyrroles may be unsubstituted or substituted one or more times with the same or different substituents (e.g., to provide an ABCD porphyrin, in which A, B, C, and D represent different substituents). The linear tetrapyrrole may be used in the form of a metal complex, or boron complex, as discussed further herein.

Any suitable metal salt can be used, depending on the metal desired in the metalloporphyrin, with particular embodiments including but not limited to magnesium, zinc, copper, palladium, nickel and indium salt. In some embodiments, magnesium halides are particularly preferred.

Suitable protecting groups include, for example, halo, thio, acetate, sulfonate, and triflate protecting groups.

Reaction conditions are not critical. In some embodiments the reaction is carried out under basic conditions (e.g., with a suitable base such as NaOH, ethylmagnesium bromide, 2-mesityl magnesium bromide, 2,2,6,6-tetramethylpiperidine, tetramethylguanidine, etc) added to the reaction mixture). The reaction may be solventless or may be carried out in a solvent. The solvent, if used, is typically an organic solvent (including mixtures), examples including ethanol, tetrahydrofuran (THF), valeronitrile, isovaleronitrile, butyronitrile, acetonitrile, xylene, mesitylene, chlorobenzene, dichlorobenzene, dichloromethane, chloroform, and toluene. The choice of specific solvent will depend upon the choice of metal salt, with some metals such as magnesium requiring a non-coordinating solvent such as toluene or chlorobenzene. In some preferred embodiments the reaction is carried out in a non-coordinating solvent such as toluene in the presence of a non-nucleophilic base such as 1,8-diazabicyclo[5.4.0]-undec-7-ene (or "DBU").

The reaction is preferably carried out in the presence of an oxidant, such as air (e.g., an open-atmosphere reaction without the inclusion of an additional chemical oxidant beyond ambient oxygen). The reaction may be carried for any suitable time (e.g., from one hour to two days) and at any temperature, including room temperature and elevated temperatures (e.g., from room temperature or 25° C., up to 70, 100 or 200° C.), and/or with microwave irradiation, with any suitable concentration of reactants (e.g., 10 or 20 up to 500 or 1000 mM, with 100-200 mM currently preferred).

Examples of porphyrins that can be made by the present invention include, but are not limited, to compounds of Formula I:

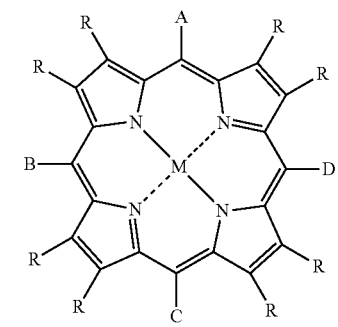
(I)

Linear tetrapyrroles that can be used to carry out reactions of the present invention include, but are not limited to, compounds of Formula IIa, IIb, IIc, IId, IIe, and IIf:

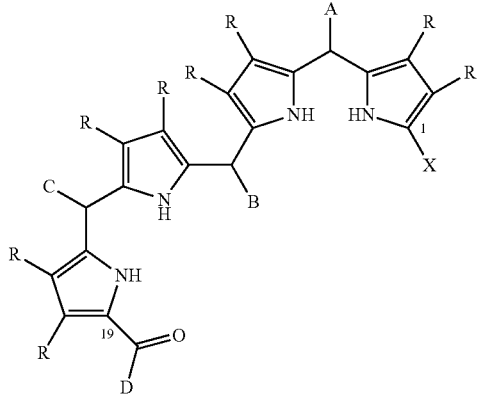
(IIa)

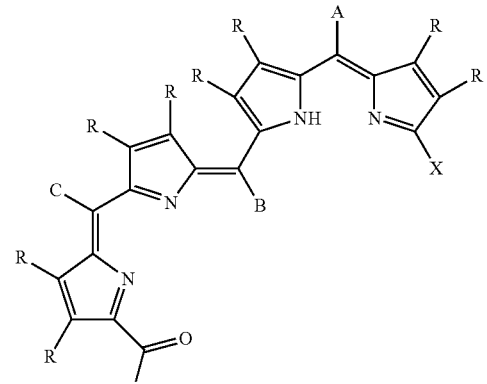
(IIb)

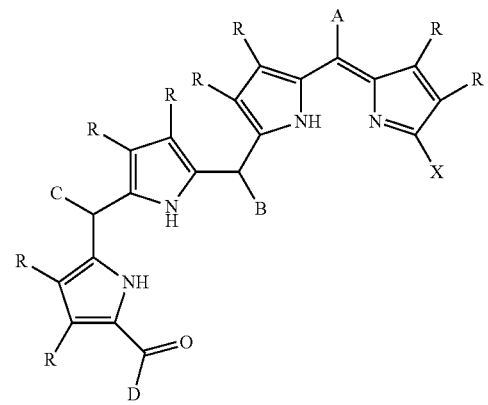
(IIc)

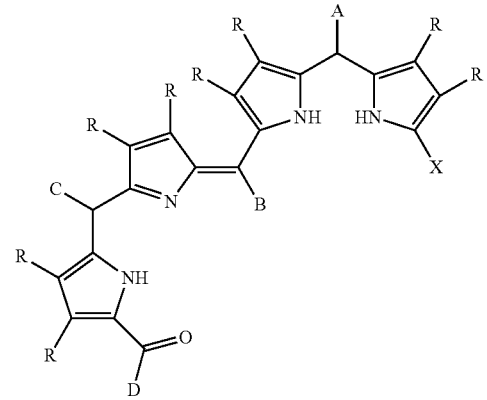
(IId)

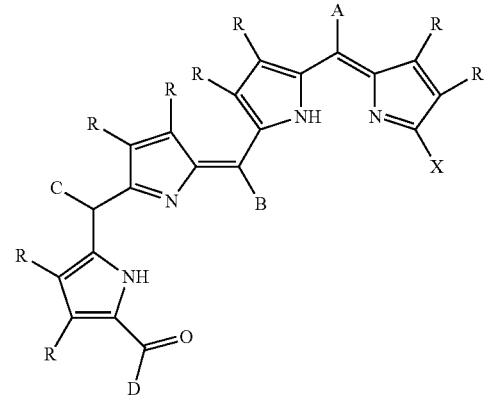
(IIe)

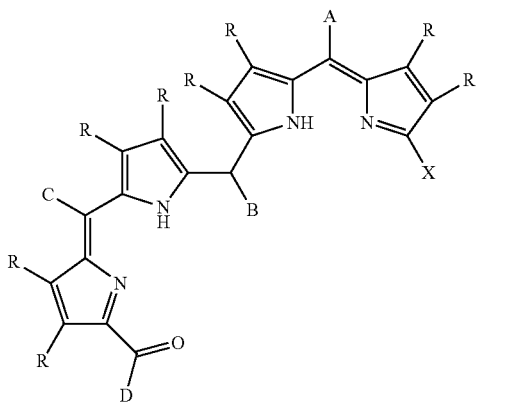

(IIf)

wherein, each A, B, C, D and R is as given above; and X is a protecting group as described above.

Compounds such as compounds of Formulas IIb-IIf as described herein are intended to include all enantiomeric and diastereomeric forms thereof unless specified otherwise. Such isomers include cis and trans isomers owing to the carbon-carbon double bond that encompasses the pyrrolenine alpha carbon and the meso carbon, and stereoisomers owing to the presence of four different substituents at a given saturated meso carbon.

Compounds of Formulas IIb-IIf can be produced by dehydrogenation (or oxidation) of compounds of Formula IIa in accordance with known techniques.

Compounds such as compounds of Formulas IIb-IIf as described herein also encompass all tautomeric forms thereof unless specified otherwise. Such tautomeric forms stem from exchange of pyrrole and pyrrolenine units in conjugated motifs along the tetrapyrrole unit.

C. Complexes of Linear Tetrapyrroles

Metal complexes. A further aspect of the invention is a complex of (i) a metal and (ii) a linear tetrapyrrole, preferably where the linear tetrapyrrole has a 19-acyl group substituted thereon, and where said linear tetrapyrrole is at least partially unsaturated (e.g., is a bilin, bilene, or biladiene). The complex can be contain any suitable metal, such as magnesium, zinc, copper, palladium, nickel, or indium. Such complexes can be made in accordance with the procedures described in Scheme 7 below (or variations thereof that will be apparent to those skilled in the art), and such complexes are also useful as intermediates for making porphyrin compounds as described in Scheme 7 (or variations thereof that will be apparent to those skilled in the art) and in the reactions for producing compounds of Formula I as described above.

Boron complexes. Linear tetrapyrroles of the invention (e.g., those having a 19-acyl group substituted thereon) can be provided in the form of a boron complex (such as shown in Scheme 6 below). Such a complex has the formula $DMR^1R^2$, wherein: D is a linear tetrapyrrole having a 19-acyl group substituted thereon (e.g., a linear tetrapyrrole as described herein), M is boron, and $R^1$ and $R^2$ are each independently selected from the group consisting of alkyl, alkenyl, alkynyl, and aryl, each of which can be unsubstituted or substituted one or more times with a substituent selected from the group consisting of alkyl, alkenyl, alkynyl, aryl, alkoxy, alkylcarbonyl, alkylcarbonyloxy, alkylsulfinyl, alkylsulfonyl, alkylthio, halo, cyano, nitro, sulfo, oxo, formyl, azido, and carbamoyl. It is to be understood that upon complexation, the linear tetrapyrrole loses a proton (from the N—H) to give D in the $DMR^1R^2$ complex. It is also to be understood that $R^1$ and $R^2$ can be covalently joined to one another if desired, as long as a covalent bond from a carbon to the boron is provided by each. Such complexes can be made in essentially the same manner as described in U.S. Pat. No. 7,153,975 to Lindsey et al., titled "Boron complexation strategy for use in manipulating 1-acyldipyrromethanes." Such boron complexes can be provided in solid form if so desired, and such complexes are useful as intermediates for making porphyrin compounds as described herein.

D. Methods of Making Linear Tetrapyrroles

Linear tetrapyrroles useful for carrying out the reactions described above can be made in accordance with known techniques, techniques as described herein, or variations thereof that will be apparent to those skilled in the art. In some embodiments, the present invention provides a method of making a compound of Formula IIa:

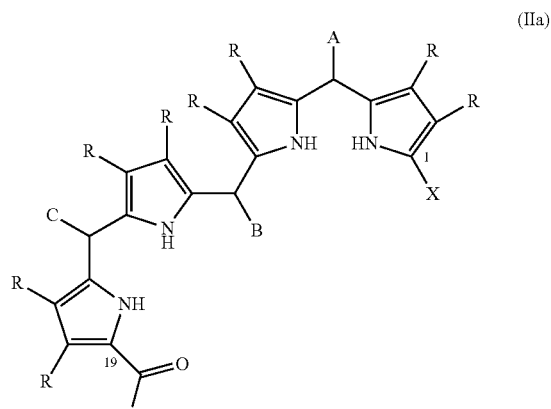

(IIa)

comprising reacting a compound of Formula III with a compound of Formula VII:

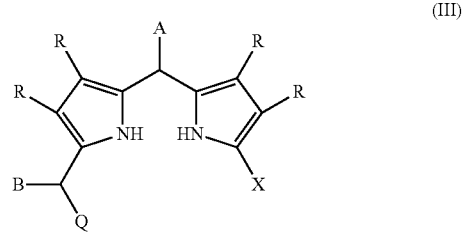

(III)

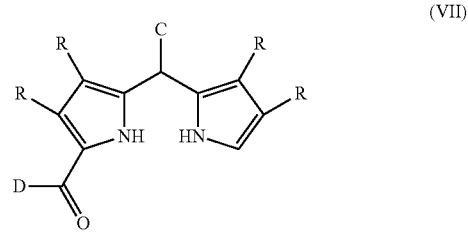

(VII)

to produce the compound of Formula IIa, where Q is a leaving group (e.g., a hydroxyl, acetate, trifluoroacetate, sulfonate, triflate or mesylate leaving group), and X, A, B, C, D, and each R is as described above.

The reaction conditions are not critical. In some embodiments the reaction is carried out by acid catalysis; in some embodiments the reaction is carried out by basic catalysis, and in some embodiments (particularly those employing a potent leaving group "Q") the reaction is carried out without catalysis. When a catalyst is employed, any suitable Lewis or Bronsted acid, or base, can be used. The reaction may be carried out at any suitable temperature, e.g., from −78° C. to 120° C., or more, and conveniently is carried out at room temperature. The reaction may be carried out in a solvent, such as a polar or nonpolar solvent organic solvent, examples including toluene, acetonitrile and dichloromethane. Acetonitrile is currently preferred. Each reactant may be included in the reaction in any suitable amount, e.g., from 100 mM to 1 M of each.

Compounds of Formula III as described above can be made by reducing a compound of Formula IV

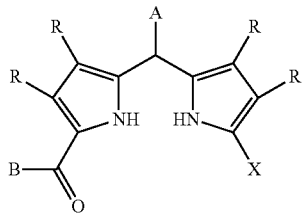

(IV)

to produce said compound of Formula III, wherein X, A, B, and each R are as described above. The reduction may be carried out under any suitable reducing conditions, such as with $NaBH_4$ or a similar reductant. Compounds of Formulas III and IV where X is halo are described in U.S. Pat. No. 6,946,552 to Lindsey et al., titled "Refined Routes to Chlorin Building Blocks".

F. Utility

Linear tetrapyrroles as described herein, including complexes thereof as described herein, are useful as intermediates for making porphyrin compounds as described herein, and particularly ABCD porphyrin compounds as described herein. Porphyrin compounds as described herein are useful for a variety of purposes, including but not limited to: as charge storage groups in information storage devices; as detectable groups in a variety of detection techniques; and as chromophores in solar cells, light harvesting rods and light harvesting arrays; as discussed further below.

Information storage devices. Porphyrin compounds described herein are useful immobilized to a substrate for making charge storage molecules and information storage devices containing the same, either individually or as linked polymers thereof, either optionally including additional compounds to add additional oxidation states. Such charge storage molecules and information storage devices are known and described in, for example, U.S. Pat. Nos. 6,208,553 to Gryko et al.; 6,381,169 to Bocian et al.; and 6,324,091 to Gryko et al. The bacteriochlorins of the invention may comprise a member of a sandwich coordination compound in the information storage molecule, such as described in U.S. Pat. No. 6,212,093 to Li et al. or U.S. Pat. No. 6,451,942 to Li et al.

Detection techniques. Porphyrin compounds as described herein can be detected by any suitable technique and hence used as detectable groups in a variety of techniques, including but not limited to flow cytometry, fluorescence spectroscopy, with a multi-well fluorescent plate scanner, scanning cytometry, fluorescent or immunofluorescent microscopy, laser scanning cytometry, bright field base image analysis, capillary volumetry, manual cell analysis and automated cell analysis. See, e.g., U.S. Pat. Nos. 5,314,805; 6,551,788 and 6,623,982.

Solar cells, light harvesting rods and light harvesting arrays. Porphyrin compounds described herein may be used as chromophores (also referred to as photosensitizers or simply sensitizers) in solar cells, including but not limited to high surface area colloidal semiconductor film solar cells (Gratzel cells), as described in, for example, U.S. Pat. Nos. 5,441,827; 6,420,648; 6,933,436; 6,924,427; 6,913,713; 6,900,382; 6,858,158; and 6,706,963. Compounds described herein may be used as chromophores in the light harvesting rods described in U.S. Pat. Nos. 6,407,330 and 6,420,648 (incorporated herein by reference). The light harvesting rod may comprise one or more porphyrin compound coupled to one or two adjacent chromophores depending upon the position thereof in the light harvesting rod. Such light harvesting rods may be utilized to produce light harvesting arrays as described in U.S. Pat. No. 6,420,648 and solar cells as described in U.S. Pat. No. 6,407,330.

The present invention is explained in greater detail in the following experimental section set forth below, which is to be construed as illustrative and not limiting of the invention.

EXPERIMENTAL

Our strategy has centered on developing a new route for constructing the porphyrinic macrocycle that does not require formation of a porphyrinogen intermediate. One approach we have pursued is to prepare a linear tetrapyrrole-carbinol for cyclization under metal-templating conditions. The advantage of this approach is that intramolecular cyclization can be favored over competing polymerization by virtue of metal-templating, which juxtaposes the reactant groups for cyclization. The use of a metal template requires pyrromethene rather than pyrromethane species for coordination (metal templating of a pyrrole itself does not occur[24]). Accordingly, oxidation of the tetrapyrrole species must precede or accompany metal templating.

This strategy requires access to bilane-carbinols, which heretofore have not, been generally accessible. The synthesis of a bilane from dipyrromethane precursors requires that one α-pyrrolic site in each dipyrromethane be masked (group z) to prevent self-condensation and/or polymerization (Scheme 2). One dipyrromethane (VII) is masked at the 1-position with an α-acyl moiety (which will become the carbinol in the bilane) and has a free α-pyrrolic site at the 9-position. The second dipyrromethane (VIII), which bears a 1-carbinol group for bilane formation, requires an α-pyrrolic protecting group (z) at the 9-position. Several α-pyrrolic protecting groups (z) were investigated for complementary dipyrromethane VIII, including the thiocyanato, alkylthio, and bromo groups.

Stepwise ABCD-Porphyrin Synthesis (General Overview)
Scheme 2 (part 1 of 2)

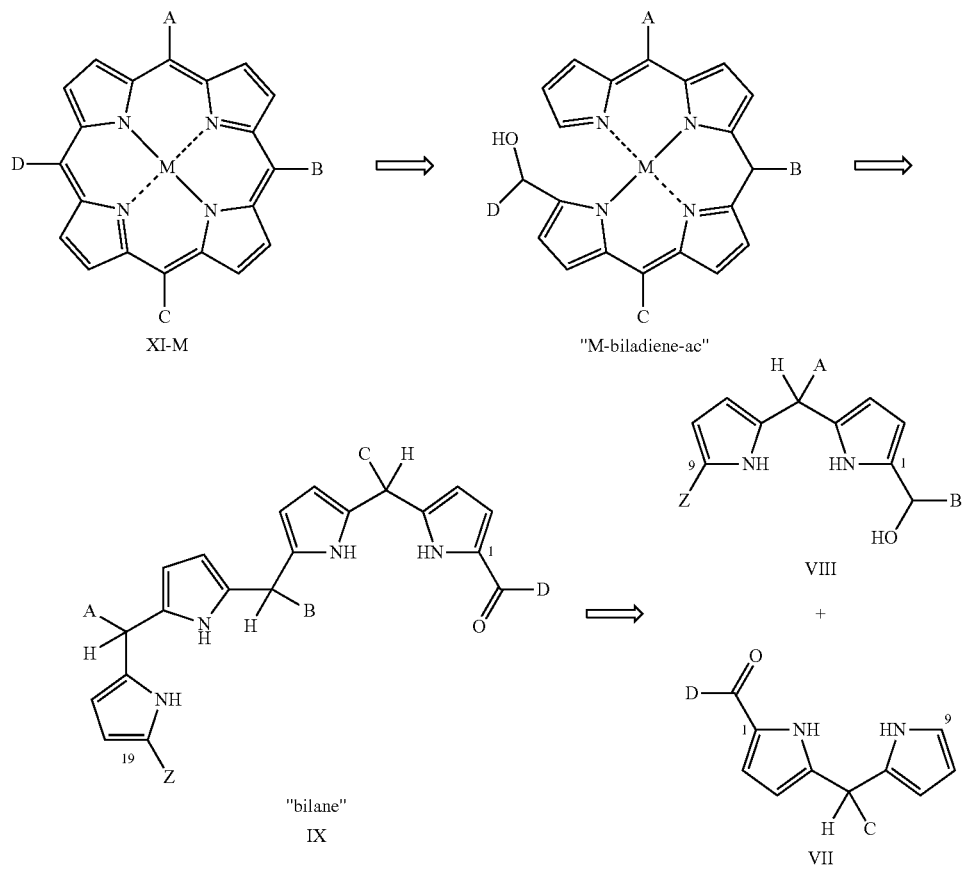

On-flash ABCD-Metalloporphyrin Synthesis
Scheme 2 (part 2 of 2)

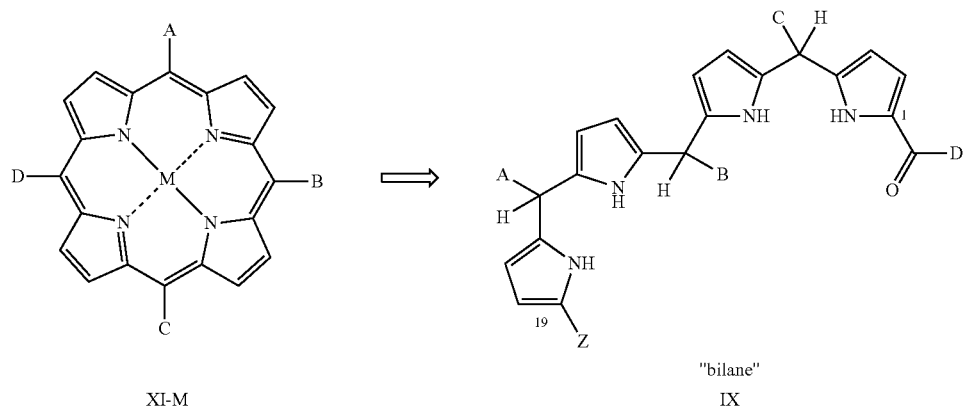

Upon preparing bilanes (IX) bearing an acyl moiety at the 1-position and a protecting group (z) at the 19-position (e.g., thioethyl), we began carrying out transformations to yield the porphyrin. The individual steps in the transformation included (i) oxidation to give the biladiene, (ii) metal complexation, (iii) desulfurization, and (iv) reduction of the acyl moiety to give the metal-templated biladiene-carbinol (X), which upon (v) acid-catalyzed condensation and (vi) oxidation would give the free base or metalloporphyrin. During the course of this work, we made the astonishing finding that the 1-acyl-19-thioethylbilane (IX, z=EtS) would undergo transformation in a direct one-flask process to give the porphyrin, thereby obviating the individual stepwise transformations. Moreover, the one-flask transformation occurred under basic conditions and yielded the metalloporphyrin.

We here describe our studies of this new route to ABCD-porphyrins. The porphyrin (XI) chosen for demonstration of the methodology contains four different meso substituents (phenyl, p-tolyl, p-ethylphenyl, and p-tert-butylphenyl), each of which is electron rich and differs in mass. The electron-rich substituents were chosen to accentuate scrambling. The mass difference was important to enable identification of possible scrambling upon LD-MS analysis. We first describe the synthesis of 1-acyldipyrromethanes bearing an α-pyrrolic protecting group at the 9-position. We then describe the synthesis of 1-acyl-19-protected bilanes by reaction of a 1-acyldipyrrnmethane and a 1-acyl-9-protected dipyrromethane. One lengthy section delineates our studies concerning the stepwise conversion of the 1-acyl-19-protected bilane to the porphyrin. The stepwise process entails the six steps (i-vi) listed above, which has provided insight into the properties and reactivity of a variety of novel tetrapyrrolic species. The final section describes the one-flask conversion of the 1-acyl-19-protected bilane to the porphyrin, which provides an ideal method for preparative applications. Taken together, the new route described herein should enable synthesis of porphyrins in good yield and at reasonable concentrations, thereby facilitating large-scale syntheses.

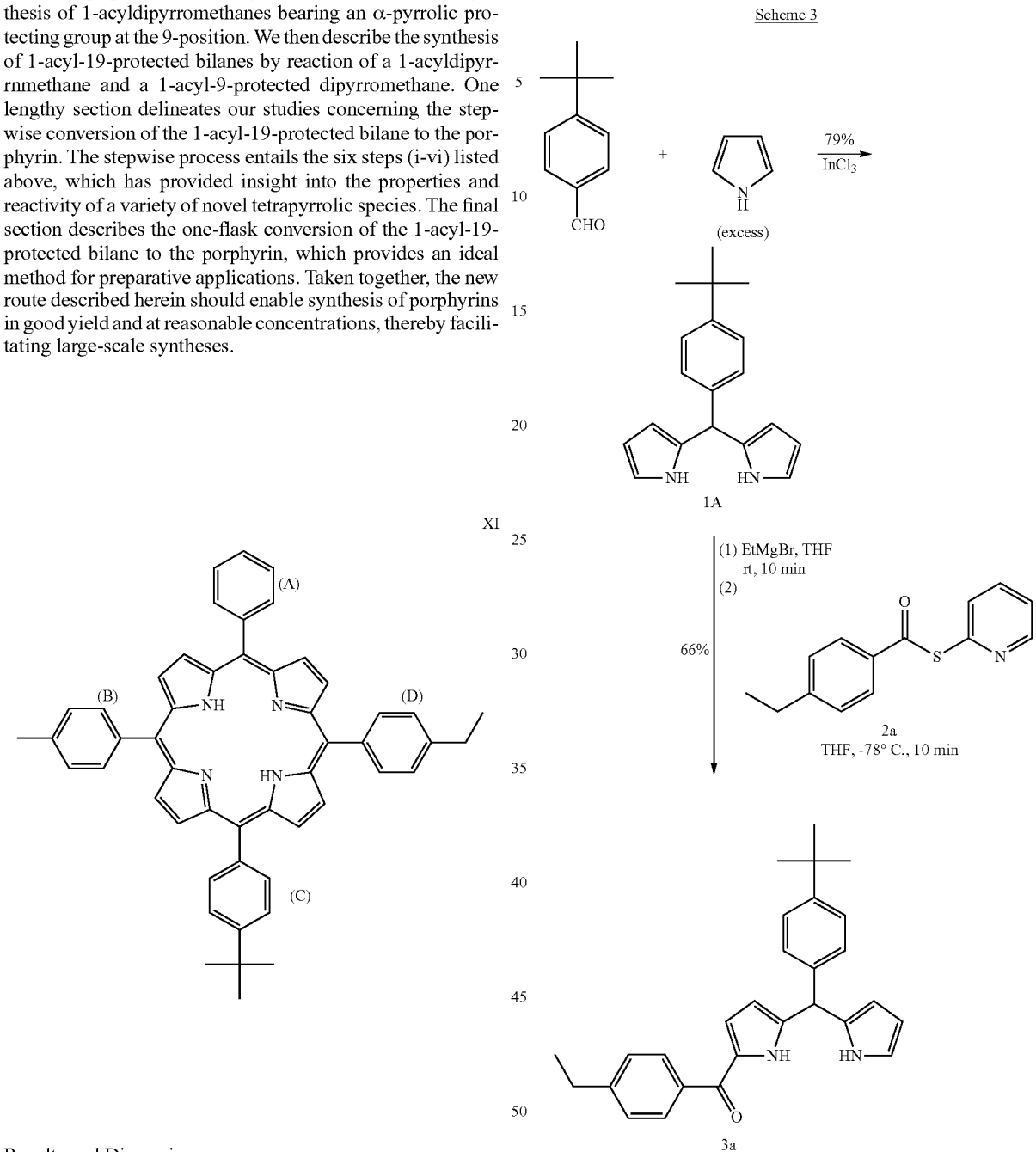

Results and Discussion

I. Synthesis of Bilanes. The initial approach focused on use of a 1-acyldipyrromethane and a 1-acyl-9-protected dipyrromethane as precursors to the target bilane. Initially we investigated thiocyanato and alkylthio groups to mask the 9-position, but later turned to the bromo atom as well. Multigram quantities of dipyrromethanes[8] and 1-acyldipyrromethanes[2] can easily be synthesized at high concentration with limited or no chromatography. Thus, the condensation of p-tert-butylbenzaldehyde with excess pyrrole afforded dipyrromethane 1a in 79% yield. Acylation of 1a with Mukaiyama reagent 2a gave the corresponding 1-acyldipyrromethane (3a) as shown in Scheme 3. Dipyrromethanes bearing alkylthio groups[3] or bromo groups[5] at the 1- and 9-positions have been prepared, but no β-unsubstituted dipyrromethanes bearing one such substituent at an α-position have been prepared.

A second 1-acyldipyrromethane (3b) was treated with ammonium thiocyanate and iodine to give the 1-acyl-9-thiocyanatodipyrromethane (4). Attempts to use this species in the synthesis of a bilane encountered difficulties owing, apparently, to loss of the cyano group upon reduction of the acyl unit. Condensation of the resulting putative 9-thiodipyrromethane-1-carbinol with 1-acyldipyrromethane 3a did not provide the expected bilane. Accordingly, the thiocyanato group was converted by treatment with EtMgBr (3 equiv) to the corresponding ethylthio unit affording the 1-acyl-9-(ethylthio)dipyrromethane (5-SEt, Scheme 4). Excess EtMgBr is necessary because dipyrromethanes possess two relatively acidic pyrrolic protons.

Scheme 4

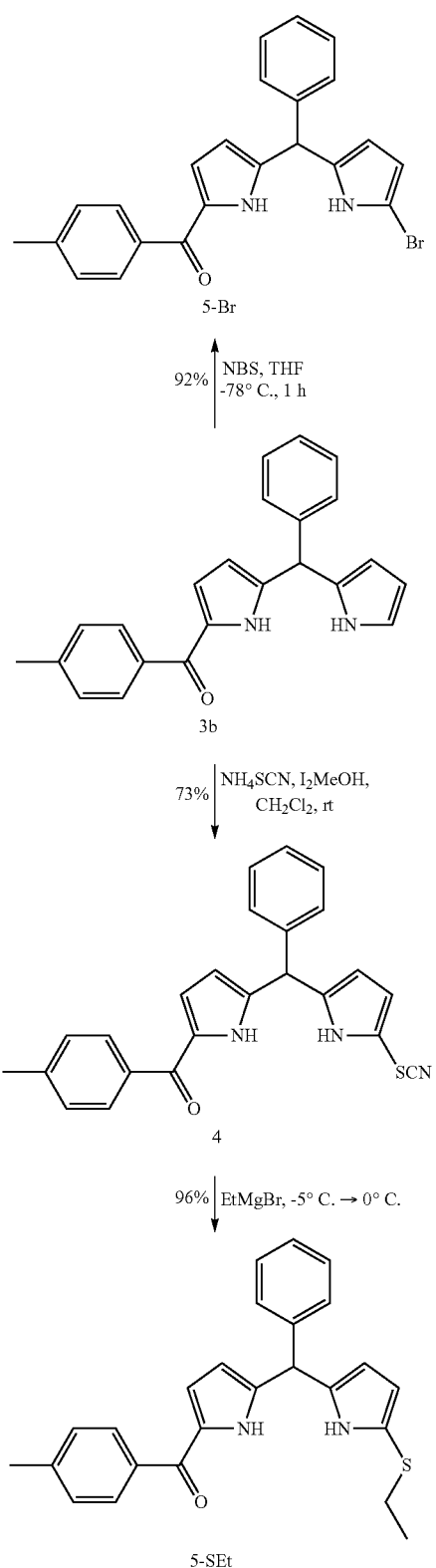

(anhydrous) at 25 mM in the presence of Sc(OTf)$_3$ (3.25 mM) and DTBP (32.5 mM) under argon, conditions developed recently for "2+2 type" porphyrin syntheses.[1] After 20 min, TLC analysis revealed complete consumption of 5-SEt-OH and a trace amount of 3a. Workup by quenching with excess TEA and column chromatography provided bilane 6-SEt in 72% yield (Scheme 5). Characterization of the bilane was performed by NMR spectroscopy ($^1$H NMR, $^{15}$N NMR, $^{13}$C NMR), LD-MS, and elemental analysis.

Scheme 5

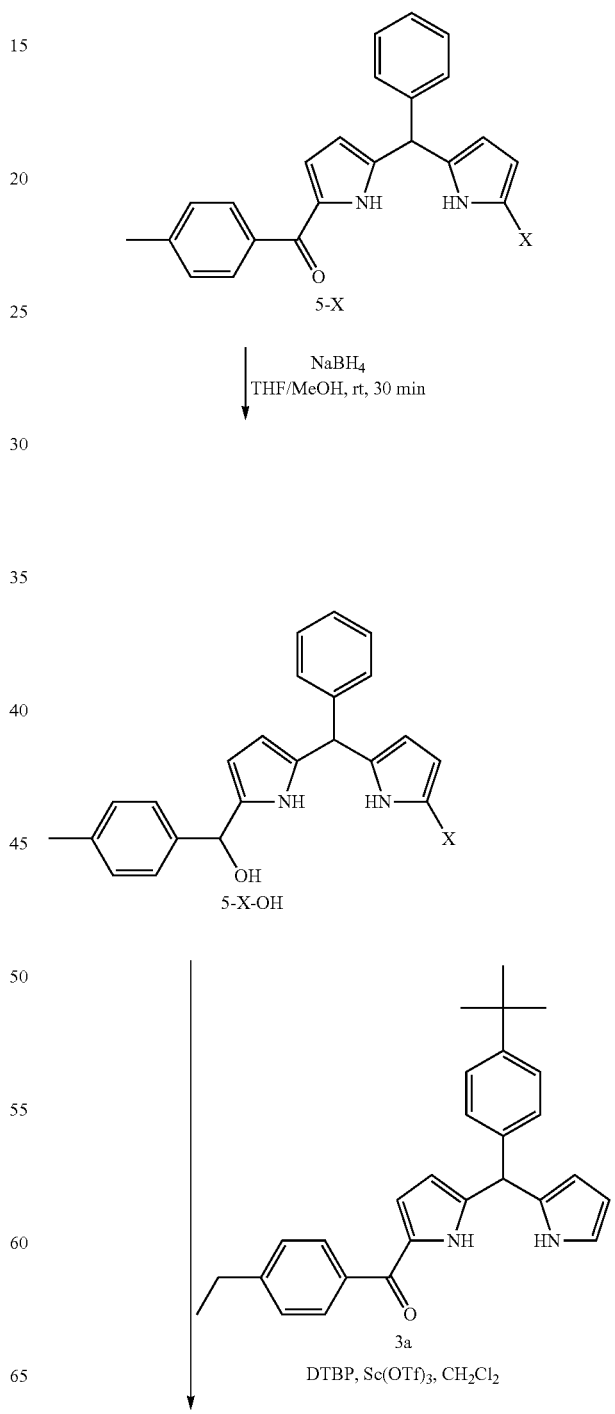

The reduction of 5-SEt to the corresponding carbinol 5-SEt-OH was performed in THF/methanol (3:1) using 25 mol equiv of NaBH$_4$. The condensation of the crude 5-SEt-OH with 1-acyldipyrromethane 3a was carried out in CH$_2$Cl$_2$

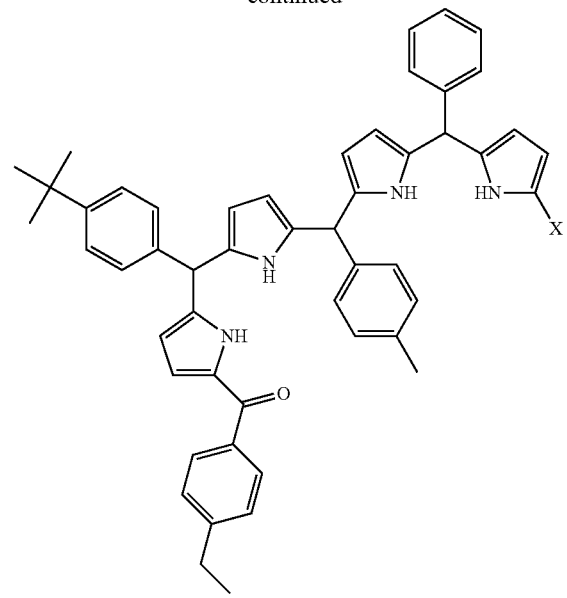

| (X) | Concentration (mM) | Yield (%) |
|---|---|---|
| —SEt | 25 | 72 |
| —Br | 500 | 35 |

6-X

We also prepared a bilane that bears a 19-bromo substituent, given the better leaving group character of —Br versus —SEt as well as our extensive experience with the preparation of the precursor 1-acyl-9-bromodipyrromethanes in chlorin syntheses.[14] Bilane 6-Br was prepared by following the same procedure that we established for bilane 6-SEt. The reduction of diyrromethane 5-Br[5] to the corresponding carbinol 5-Br—OH was performed in THF/methanol (3:1) using 25 mol equiv of $NaBH_4$. The condensation of the crude 5-Br—OH with 1-acyldipyrromethane 3a was carried out in $CH_2Cl_2$ (anhydrous) at 500 mM in the presence of $Sc(OTf)_3$ (3.25 mM) and DTBP (32.5 mM) under argon. After 10 min, TLC analysis showed complete consumption of 5-Br—OH and only a trace of 3a, and no further change was observed upon stirring for a further 40 min. Standard workup including column chromatography provided bilane 6-Br as a brown foam in 35% yield (Scheme 5). Characterization of the bilane 6-Br was performed by NMR spectroscopy ($^1$H NMR, $^{15}$N NMR, $^{13}$C NMR), LD-MS and FAB-MS. The NMR spectral results were consistent with the bilane species. The high resolution exact mass spectrum of putative 6-Br gave a peak at m/z=811.3035, consistent with an elemental composition of $C_{51}H_{48}BrN_4O$ (calcd 811.3011). The observed peak is consistent with the protonated molecule ion derived from the $2e^-/2H^+$-oxidized analogue of 6-Br. Bilanes are known to be prone to oxidation,[6] which may have occurred during the mass spectrometric process.

For further characterization purposes, the bilane 6-Br was converted to the corresponding 9-BBN complex, mirroring chemistry we have employed for the boron complexation of 1-acyl dipyrromethanes.[17] The dialkylboron complexes of 1-acyldipyrromethanes are much more hydrophobic than the parent acyldipyrromethanes and crystallize easily, thereby facilitating isolation. Treatment of 6-Br with TEA in toluene followed by addition of 9-BBN afforded 6-Br—BBN in 80% yield (Scheme 6). Spectral characterization of 6-Br-BBN was consistent with the proposed structure, again indicating the integrity of the bilane unit.

Scheme 6

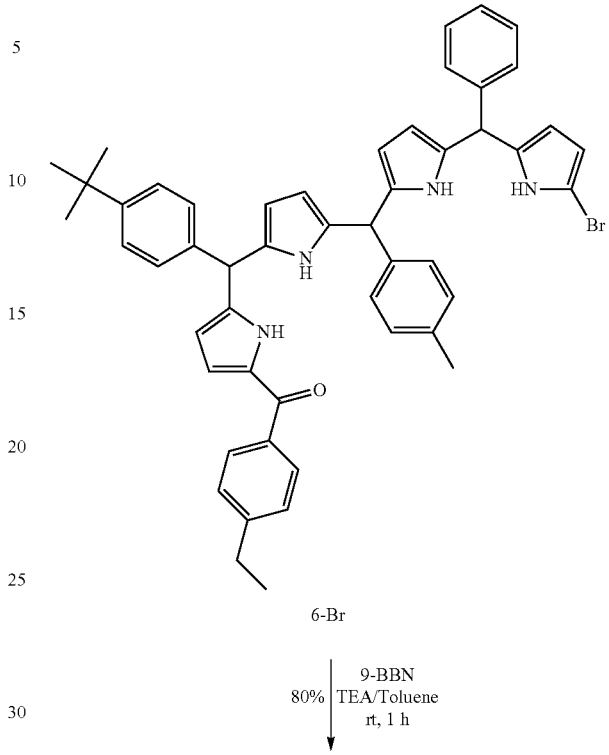

6-Br

80% | 9-BBN
TEA/Toluene
rt, 1 h

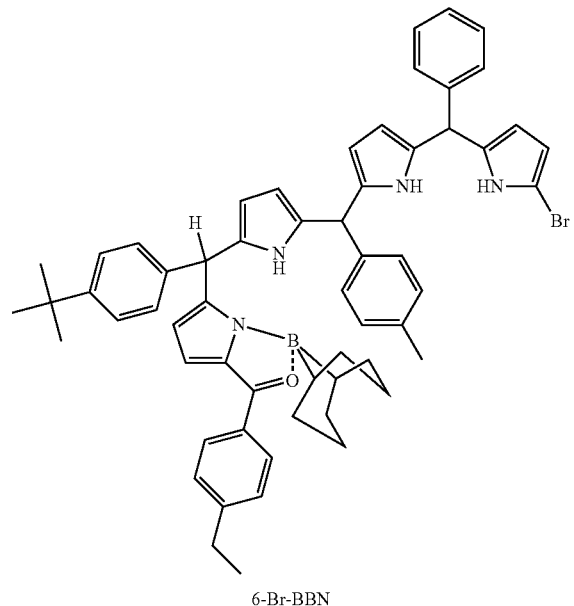

6-Br-BBN

Bilanes 6-SEt and 6-Br were found to be stable in the solid state at −15° C. for at least several weeks. Partial decomposition was observed upon dissolution of bilanes 6-X in chlorinated solvents for 3-5 hours on the bench top.

II. Stepwise Synthesis of ABCD-Porphyrins (i) Exploration of Metal Salts as Templates for ABCD-porphyrin Formation. We examined ABCD-porphyrin formation from bilane 6-SEt in the presence of a metal reagent. The porphyrin formation was performed in a stepwise manner including (i) oxidation/metalation, (ii) desulfurization, (iii) reduction, and (iv) ring closure (Scheme 7). Putative intermediates (e.g., 7-M, 8-M, 8-M—OH) were not purified. In all trials the final condensation was performed at 100 mM. In this study seven metal salts [$MX_2$=$MgI_2$, $Co(OAc)_2$, $NiCl_2$, $Cu(OAc)_2$, $Zn(OAc)_2$, $Pd(OAc)_2$, $Sn(OAc)_2$] were examined and carried through the process.

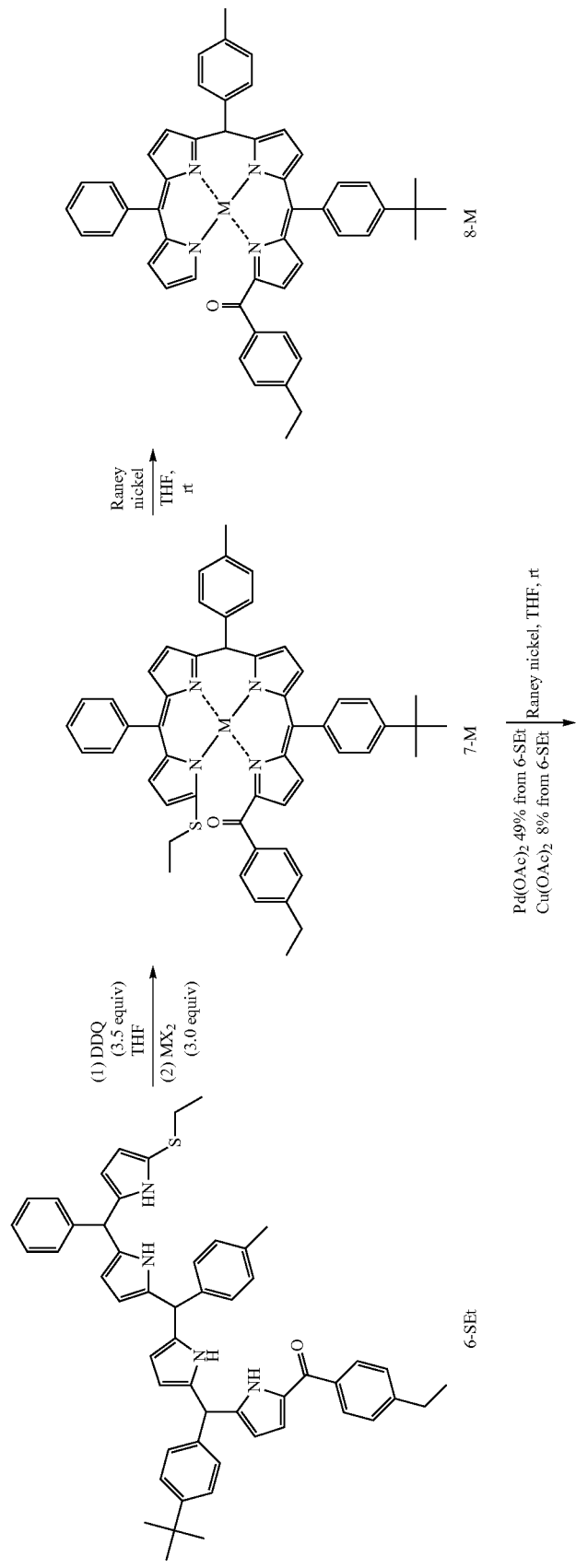

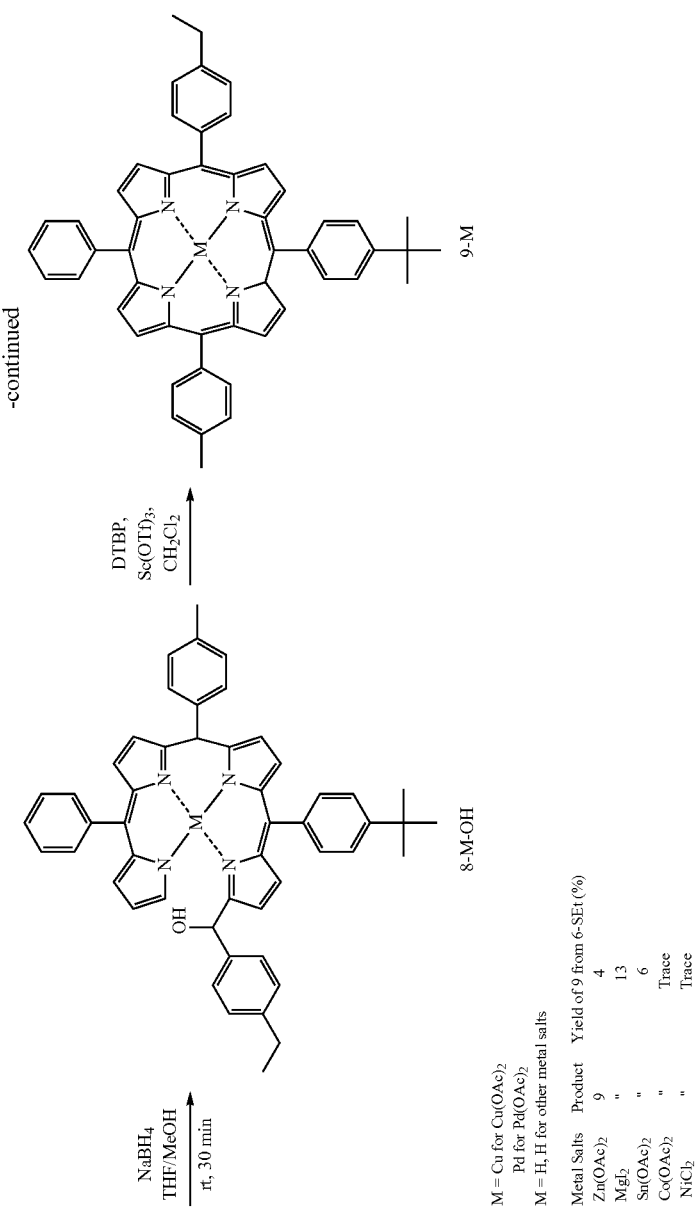

Step One: Oxidation and Metalation of Bilane 6-SEt. Treatment of bilane 6-SEt (50 mM) with DDQ (3.5 equiv versus 6-SEt) at room temperature in THF (Scheme 7) caused the reaction mixture to change immediately from light yellow to dark green. The absorption spectrum of the crude reaction mixture showed three bands (348, 443 and a broad band at 592 nm). LD-MS of the crude reaction mixture gave a peak at m/z 789.5 consistent with the corresponding free base biladiene-ac. The crude biladiene-ac was treated in situ with excess metal salt $MX_2$ (3 equiv versus 6-SEt). The reaction mixture darkened slowly, affording a broad peak at ~490 nm (not shown) having a putative structure consistent with the data corresponding to:

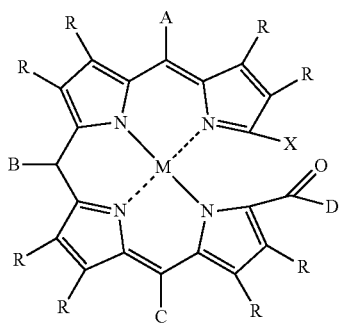

where (depending upon the choice of starting linear tetrapyrrole as described herein), each A, B, C, D, R, and X is as described above).

Each crude sample was analyzed by LD-MS whereupon the expected molecule ion peak was observed. The reaction mixture was neutralized by addition of TEA (10 mol equiv versus metal salt), and aqueous workup was performed. The biladiene-ac metal salts were isolated and found to be stable in the solid state at −15° C. for several weeks. In general, the product was not purified, but the crude reaction mixture was used in the next step without purification. The zinc(II)-biladiene-ac complex was characterized in detail, and the data are listed below.

The $^1$H NMR spectrum illustrates (1) loss of four pyrrolic NH resonances found in the bilane precursor (11.86, 10.91, 10.51, and 10.40 ppm in DMSO-$d_6$), (2) loss of 2 of 3 meso protons (5.26, 5.32 ppm in CDCl$_3$, bilane pyrrolic NH possess four different chemical shifts in DMSO-$d_6$ and three meso protons can be distinguished in CDCl$_3$), (3) $^{13}$C NMR spectroscopy revealed two meso carbons which possesses chemical shifts at 115.55 and 115.88 ppm (in CDCl$_3$, tentatively assigned as C5 and C15) which are consistent with the chemical shift of meso carbon atoms in dipyrrinic compounds,[7] (4) the third meso carbon (tentatively assigned as C10) has a $^{13}$C chemical shift at 34.89 ppm as expected for the meso carbon in dipyrromethanes.[8]

The absorption band at 490 nm was consistent with that of meso unsubstituted biladiene-ac metal complexes,[9] and can be contrasted with the spectra of meso unsubstituted bilene-b metal complexes (~235, 392 and 500 nm),[10] the protonated bilene-b (broad band at ~505 nm),[11] the bilatriene-abc salt (~420 and 750 nm), and a free base bilatriene-abc (~400 and 680 nm).[12] To our knowledge, there are no reports of bilatriene-metal complexes (although metal complexes have been reported for the structurally quite different biliverdin[16]).

Step Two: Desulfurization of 7-M, Affording 8-M. Desulfurization of the biladiene-ac metal complex 7-M was carried out according to a reported procedure for 1,9-bis(alkylthio)dipyrromethanes[3] (Scheme 7). A solution of 7-M in THF (5.0 mL, 12.5 mM) was treated with Raney nickel for one hour. LD-MS analysis of the crude mixture gave a peak attributed to the desulfurized biladiene product accompanied by demetalation for Mg(II), Co(II), Ni(II), Zn(II), and Sn(II). In each case only partial desulfurization occurred; regardless, the crude product was used in the next step without purification. For Cu(II) or Pd(II), attempted desulfurization with Raney nickel gave, surprisingly, not the biladiene, but the metalloporphyrin in 8% and 49% yield, respectively.

Step Three: Synthesis of Metalated Biladiene-ac Carbinol 8-M—OH. Reduction of the biladiene-ac metal complex 8-M was performed according to the modified procedure reported for diacyldipyrromethanes.[1] Thus, treatment with NaBH$_4$ (25 mol equiv) in THF/MeOH (3:1) afforded the carbinol 8-OH (Scheme 7). LD-MS analysis of the crude reaction mixture did not show a peak corresponding to the starting material, but showed peaks corresponding to the carbinol and a presumed fragment lacking the OH.

Step Four: Porphyrin Synthesis. The crude free base biladiene-carbinol 8-OH (obtained from each of the five $MX_2$ that results in demetalation upon desulfurization; vide supra) in anhydrous $CH_2Cl_2$ was treated with Sc(OTf)$_3$ (3.25 mM) in the presence of 2,6-di-tert-butylpyridine (DTBP, 32.5 mM). The acid-catalyzed condensation was performed with the sample of 8-OH set equal to 100 mM, assuming quantitative yields in each of steps 1-3. After 20 min, the absorption spectrum showed a strong band at 419 nm, corresponding to the Soret band of the free base meso-tetraarylporphyrin. The LD-MS spectrum of the purified sample was consistent with free base porphyrin 9 (Scheme 7). The isolated yield of porphyrin from each sample of biladiene 8-OH ranged from 4-13% (from 6-SEt). The origin of the variation in yields is not known, and can stem from any of the four steps. The highest yield (13%) was obtained with MgI$_2$.

III. One-Flask Synthesis of Metalloporphyrins from Bilanes (6-Br, 6-SEt). Recently we serendipitously discovered a new one-flask route to meso-substituted porphyrins by reaction of an acyldipyrromethane in the presence of a palladium (or copper) reagent under basic aerobic conditions. The reaction of a 1-acyldipyrromethane in this manner affords the corresponding trans-$A_2B_2$-metalloporphyrin.[5] The direct route to such metalloporphyrins is more practical than the analogous prior synthesis of porphyrins, obviating the following steps: (1) reduction of the 1-acyldipyrromethane, (2) acid-catalyzed condensation, (3) oxidation of the porphyrinogen intermediate with a high-potential quinone, and (4) metal insertion. This route also could be used for the reaction of a 1,9-diacyldipyrromethane and a dipyrromethane. However, all attempts failed to extend this approach to metals other than palladium or copper.

We investigated this approach for the synthesis of ABCD-porphyrins where a bilane (6-SEt or 6-Br) was used under basic conditions. Thus, reaction of bilane 6-SEt (100 mM) in the presence of Pd(CH$_3$CN)$_2$Cl$_2$ (1.1 equiv) and KOH (5 equiv) in refluxing ethanol exposed to air afforded the corresponding palladium porphyrin 9-Pd in 29% yield (spectroscopic yield, Scheme 8, Table 1). The success of this method is remarkable, given that porphyrin formation from the bilane bearing a 19-acyl group and a 1-protective group (6-SEt) requires displacement of the alkylthio unit, formation of a carbon-carbon bond, deoxygenation, oxidation of the tetrapyrrole species, and metalation. The success of this method prompted a series of studies to explore the scope of the reaction conditions, as described in the following sections.

Scheme 8

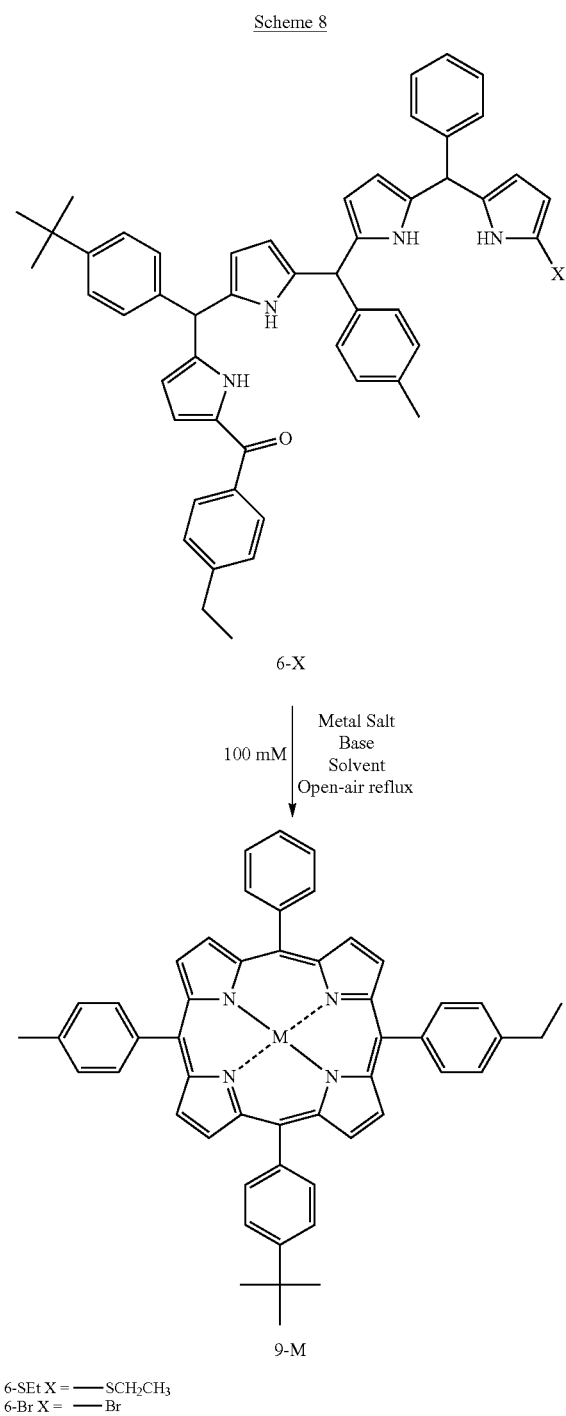

6-SEt X = —SCH₂CH₃
6-Br X = —Br

TABLE 1

Survey of Palladium Reagents for One-Flask Cyclization of Bilane 6-SEt.[a]

| Entry | Palladium reagent | Yield (%) 25 mM | Yield (%) 100 mM |
|---|---|---|---|
| 1 | Pd(CH₃CN)₂Cl₂ | 38[b] | 29[b] |
| 2 | Pd(OAc)₂ | 13 | n.a. |
| 3 | Pd(CF₃COO)₂ | 28 | n.a. |

TABLE 1-continued

Survey of Palladium Reagents for One-Flask Cyclization of Bilane 6-SEt.[a]

| Entry | Palladium reagent | Yield (%) 25 mM | Yield (%) 100 mM |
|---|---|---|---|
| 4 | PdBr₂ | 22 | n.a. |
| 5 | Pd(acac)₂ | 32 | n.a. |

[a]The standard condition employed bilane 6-SEt (0.013 mmol), KOH (5 mol equiv versus bilane 6-SEt) and palladium reagent (1 mol equiv versus bilane 6-SEt) in ethanol exposed to open-air reflux. In this study the product is 9-Pd.
[b]Yield of isolated porphyrin determined by absorption spectrometry.

(i) Investigation of Palladium Reagents. The condensation of bilane 6-SEt in the presence of a palladium reagent (1 mol equiv versus bilane 6-SEt) and base (KOH, 5 mol equiv versus bilane 6-SEt) was carried out in ethanol under open-air reflux for a variety of palladium reagents. In each case, the resulting reaction mixture was heterogeneous and the palladium porphyrin was observed as a purple film on the walls of the reaction flask. When the reaction was complete, ethanol was removed and the crude reaction mixture was dissolved in $CH_2Cl_2$. Filtration of the crude product through an alumina column afforded the palladium porphyrin 9-Pd. The results are summarized in Table 1. The yields ranged from 13-38% (25 mM reactant) and up to 29% (100 mM reactant). Among several palladium reagents, $Pd(CH_3CN)_2Cl_2$ afforded the highest yield: 38% at 25 mM, and 29% at 100 mM from bilane 6-SEt.

(ii) Investigation of Other Metal Salts and Conditions. Success of the palladium-mediated cyclization prompted us to examine other metal reagents. We explored metals that could be more easily removed than palladium from the resulting metalloporphyrin. In this study, the bilane (6-SEt or 6-Br at 100 mM) was condensed in the presence of a metal salt (2 or 15 mol equiv versus bilane 6-SEt or 6-Br) and a base (5 or 60 mol equiv versus bilane 6-SEt or 6-Br) in an appropriate solvent (ethanol, isovaleronitrile, valeronitrile, butyronitrile, acetonitrile and toluene) at reflux exposed to air. After porphyrin formation was complete, the reaction mixture was concentrated, worked up, and chromatographed to isolate any porphyrin. In this study, eight different metal species [Mg(II), Fe(II), Co(II), Ni(II), Zn(II), Cd(II), In(III), Sn(II)], four different bases, and six different solvents were explored. The results are shown in Table 2. Note that in all of the following studies, the formation of a magnesium porphyrin or zinc porphyrin was accompanied by a trace amount of free-base porphyrin (as observed by TLC, absorption spectroscopy and LD-MS analysis).

Among the eight different metal species in the reaction with KOH in EtOH (entries 1-10), a significant amount of metalloporphyrin was observed only with Ni(II), and a trace was observed with In(III).

A series of experiments was carried out in nitrile solvents (entries 11-20) with various bases and metal reagents. The combination of DBU (1,8-diazabicyclo[5.4.0]-undec-7-ene) and acetonitrile did not provide complete disappearance of an intermediate (~470 nm, entries 11-14). Reactions in butyronitrile, isovaleronitrile, or valeronitrile (bp ~130° C.) with Mg(II), Zn(II) or In(III) in the presence of DBU afforded the corresponding metalloporphyrin in shorter time (entries 15-20).

In the studies of the stepwise synthesis, magnesium(II) appeared to give efficient formation of the metal-complexed biladiene-ac, and also gave the highest yield of porphyrin among all metal reagents other than those containing palladium. Accordingly, the reaction of 6-SEt was carried out with MgBr$_2$ and several bases in the non-coordinating solvent toluene. The bases include 1,1,3,3-tetramethylguanidine (TMG) and 2,2,6,6-tetramethylpiperidine (TMPi), both of which gave low yields of magnesium porphyrin (entries 21 and 22). No porphyrin was obtained in the absence of MgBr$_2$ with the bases ethylmagnesium bromide (1.0 M solution in THF, EtMgBr), diisopropylethylamine (DIEA), and lithium bis(trimethylsilyl)amide (1.0 M solution in hexanes, LiHMDS) (entries 23-25). Indeed, LiHMDS (5 mol equiv versus bilane 6-SEt) in dry toluene gave no porphyrin even upon stirring the reaction mixture at 110° C. for two days.

(10 mol equiv) at 100 mM prompted examination of other metal reagents under the same conditions. Four zinc salts were investigated for the synthesis of 9-Zn from bilane 6-Br at 100 mM. The results are shown in Table 4. The highest yield (50%) was obtained with Zn(OAc)$_2$. One reaction at slightly larger scale gave a 23% yield. The reaction with InCl$_3$ gave the corresponding metalloporphyrin in XX % isolated yield. Similar to the results obtained with MgBr$_2$, each zinc reagent gave the zinc porphyrin accompanied by a trace amount of free-base porphyrin (as observed by TLC, and absorption spectroscopy analysis).

TABLE 2

Survey of Metal Reagents for One-Flask Cyclization of Bilane 6-SEt.[a]

| Entry # | Metal Salt (equiv) | Base (equiv) | Solvent | Time (h) | Yield (%) | Porphyrin |
|---|---|---|---|---|---|---|
| 1 | Zn(OAc)$_2$ (2) | KOH (5) | EtOH | 48 | — | — |
| 2 | FeCl$_2$ (2) | " | " | " | — | — |
| 3 | SnCl$_2$ (2) | " | " | " | — | — |
| 4 | Co(OAc)$_2$ (2) | " | " | " | — | — |
| 5 | NiCl$_2$ (2) | " | " | " | 12[b] | 9-Ni |
| 6 | Ni(OAc)$_2$ (2) | " | " | " | 8 | 9-Ni |
| 7 | Sn(OAc)$_2$ (2) | " | " | " | — | — |
| 8 | CdCl$_2$ (2) | " | " | " | — | — |
| 9 | Fe(OAc)$_2$ (2) | " | " | " | — | — |
| 10 | InBr$_3$ (2) | " | " | " | Trace | 9-In |
| 11 | MgBr$_2$ (15) | DBU(60) | Acetonitrile | 72 | " | not complete |
| 12 | MgI$_2$ (15) | " | " | " | " | " |
| 13 | InCl$_3$ (15) | " | " | " | " | " |
| 14 | InBr$_3$ (15) | " | " | " | " | " |
| 15 | MgBr$_2$ (15) | " | Butyronitrile | 12 | 15 | 9-Mg |
| 16 | MgI$_2$ (15) | " | " | " | 10 | " |
| 17 | Mg(OTf)$_2$ (15) | DBU (30) | Isovaleronitrile | 3 | 8 | 9 |
| 18 | " | " | Valeronitrile | 6 | 9 | " |
| 19 | Zn(OTf)$_2$ (15) | " | Isovaleronitrile | " | — | — |
| 20 | InCl$_3$ (15) | " | " | 12 | Trace | 9-In |
| 21 | MgBr$_2$ (15) | TMG (60) | Toluene | " | 5 | 9-Mg |
| 22 | " | TMPi (60) | " | 24 | 2 | " |
| 23 | — | EtMgBr | Toluene | 48 | — | — |
| 24 | — | LiHMDS | " | " | — | — |
| 25 | — | DIEA | " | " | — | — |

[a]All reactions were carried out with 0.013 mmol of 6-SEt.
[b]Spectroscopic yield.

(iii) Comparison of 6-SEt and 6-Br. Bilanes 6-SEt and 6-Br were studied under identical condition to compare their reactivity. A solution of bilane 6-SEt or 6-Br in dry toluene was first treated with DBU (10 mol equiv versus 6-SEt or 6-Br) and MgBr$_2$ (3 mol equiv versus 6-SEt or 6-Br). The reaction mixture was stirred under open-air reflux. When bilane 6-Br was used, porphyrin formation was complete in 1 h affording 9-Mg in 64% yield. With 6-SEt, porphyrin formation was complete in 8 h giving 9-Mg in only 10% spectroscopic yield (Table 3). Thus, all subsequent studies were carried out with the more reactive bilane 6-Br.

TABLE 3

Comparison of Bilanes 6-SEt and 6-Br.[a]

| Entry | Scale (mmol) | Concentration [mM] | Metal Salt (equiv) | Base (equiv) | Time (h) | Yield of 9-Mg (%) |
|---|---|---|---|---|---|---|
| 6-SEt | 0.025 | 100 | MgBr$_2$ (3) | DBU (10) | 8 | 10[b] |
| 6-Br | 0.025 | 100 | MgBr$_2$ (3) | DBU (10) | 1 | 64[b] |

[a]The standard condition employed treatment of a bilane (6-Br or 6-SEt) solution in toluene, first with DBU (10 mol equiv versus bilane 6-Br or 6-SEt) and then with MgBr$_2$ (3 mol equiv versus bilane 6-Br or 6-SEt). The resulting heterogenous reaction mixture was heated at open-air reflux affording 9-Mg.
[b]Yield of isolated porphyrin determined by absorption spectrometry.

(iv) Investigation of Other Metal Reagents. The 65% yield in the synthesis of 9-Mg using MgBr$_2$ (3 mol equiv) and DBU

TABLE 4

Survey of Metal Salts for One-Flask Cyclization of Bilane 6-Br.[a]

| Entry | Metal Salt (equiv) | Scale (mmol) | Conc. [mM] | DBU (equiv) | Time (h) | Product | Yield (%) |
|---|---|---|---|---|---|---|---|
| 1 | MgBr$_2$ | 0.062 | 100 | 10 | 1.5 | 9-Mg | 69 |
| 2 | Zn(OAc)$_2$ | 0.062 | 100 | 10 | 1 | 9-Zn | 50 |
| 3 | InCl$_3$ | 0.062 | 100 | 10 | n.a. | 9-InX | n.a. |
| 4 | ZnBr$_2$ | 0.025 | 100 | 10 | 5 | 9-Zn | 26[c] |
| 5 | ZnI$_2$ | 0.025 | 100 | 10 | 4 | 9-Zn | 31[c] |
| 6* | Zn(acac)$_2$ | 0.025 | 100 | 10 | 3.5 | 9-Zn | 37[c] |

[a]The standard condition employs treatment of bilane 6-Br solution in toluene first with DBU (10 mol equiv versus bilane 6-Br) and after 5 min with the corresponding metal reagent (3 mol equiv versus bilane 6-Br). The resulting heterogenous reaction mixture sonicated for a few secs, and then stirred at room temperature for 1 min. The reaction mixture was stirred and heated under open-air reflux.
[b]Zn(acac)$_2$ is soluble in toluene, hence, sonication was not performed. The yield of free base porphyrin 9 was determined to be 0.4%.
[c]Yield of isolated porphyrin determined by absorption spectrometry.

(v) Oxidation Conditions. The balanced equation for ABCD-porphyrin synthesis directly from bilane 6-Br is shown in Scheme 9. The conversion of bilane 6-Br to the corresponding porphyrin requires a 2e$^-$/2H$^+$ oxidation. We presume that oxygen (½O$_2$) from air serves as the oxidant. Two molecules of water are formed, one from oxidation and one from condensation. The reaction also produces three equivalents of acid, one (HBr) from the bilane upon cyclization and two (HX) from the metal reagent MX$_2$ upon metalation. The formation of acid indicates the necessity for the presence of a base, otherwise the metalloporphyrin could undergo demetalation. Thus, while the base is believed to function catalytically in accelerating the reaction, several equivalents may be essential given the formation of acid during the course of porphyrin formation.

TABLE 5

Effects of Atmosphere on Porphyrin Formation.[a]

| Entry | Porphyrin Formation | Yield of 9-Mg (%) | Yield of 9 (%) |
|---|---|---|---|
| 1 | Under oxygen | 31 | 0.8 |
| 2 | Under open-air reflux | 67 | 0.6 |
| 3 | Under argon | 51 | 0.3 |

[a]The standard condition employs treatment of bilane 6-Br solution in toluene, first with DBU (10 mol equiv versus bilane 6-Br) and then with MgBr$_2$ (3 mol equiv versus bilane 6-Br). The heterogeneous reaction mixture was sonicated for a few secs, and then stirred at room temperature for 1 min. The resulting reaction mixture was stirred and heated at reflux under the specified conditions. All yields of isolated porphyrin were determined by absorption spectrometry.

(vi) Scale-up. The reaction of 6-Br in the presence of MgBr$_2$ and DBU gave the magnesium porphyrin in 65% yield. The reaction was carried out with 0.50 g (0.62 mmol) of 6-Br and afforded 0.295 g of 9-Mg. We also carried out one reaction under solventless conditions, where toluene was omitted. Thus, the reaction of 6-Br in the presence of MgBr$_2$ and DBU gave 9-Mg in 35% yield. The latter reaction conditions may prove useful at the industrial scale where the recovery of DBU for reuse may be desirable.

Experimental Section

General. $^1$H NMR spectra (400 MHz) and $^{13}$C NMR spectra (100 MHz) were collected in CDCl$_3$ at room temperature unless noted otherwise. Melting points are uncorrected. Silica gel (40 μm average particle size) was used for column chromatography. THF and toluene were distilled from sodium/benzophenone under argon. Methanol (anhydrous) and CH$_2$Cl$_2$ (anhydrous) were used as received. All other chemicals were reagent grade and were used as received. The dipyrromethanes, 1-acyldipyrromethanes, and bilanes are easily detected in TLC upon exposure to Br$_2$ vapor. LD-MS data for bilanes 6-SEt and 6-Br were obtained with a matrix. Grade V alumina was prepared by adding 15 mL of distilled H$_2$O to 85 g of alumina (Fisher A-540) with vigorous mechanical stirring.

Yield Determinations. The yield of porphyrin was determined in three ways depending on the reaction scale and experimental objective. (1) In reactions of all scales, the crude reaction mixtures often were examined by absorption spectroscopy. The resulting yield is specified as a "spectroscopic yield" determined with use of a molar absorption coefficient of a metalloporphyrin at the Soret band of 500,000 M$^{-1}$ cm$^{-1}$. This procedure permitted an assessment of yield without employing a purification procedure. This procedure has been described in detail.[25] (2) In other small-scale reactions, the porphyrin was purified and isolated by chromatography. Owing to the small quantity of solid porphyrin, gravimetry was not performed. Instead, the solid sample was dissolved in a known volume of solvent, and the yield was determined by absorption spectrometry, again using the molar absorption coefficient of a metalloporphyrin at the Soret band of 500,000 M$^{-1}$ cm$^{-1}$. When free base porphyrins were isolated, a molar absorption coefficient of at the Soret band of 430,000 M$^{-1}$ cm$^{-1}$ was employed. This procedure is referred to as the "yield of isolated porphyrin determined by absorption spectrometry". (3) Larger scale reactions afforded sufficient porphyrin for yield determination by gravimetry, which was the method employed unless specified otherwise. In some cases this method is emphasized by stating "isolated yield".

Noncommercial Compounds. 1-Acyldipyrromethane 3b[17] and 5-Br[5] were prepared as described in the literature.

5-(4-tert-Butylphenyl)dipyrromethane (1a). Following a general procedure,[8] a solution of 4-tert-butylbenzaldehyde (16.2 g, 100 mmol) in pyrrole (694 mL, 10.0 mol) at room temperature under argon was treated with InCl$_3$ (2.21 g, 10.0

Scheme 9

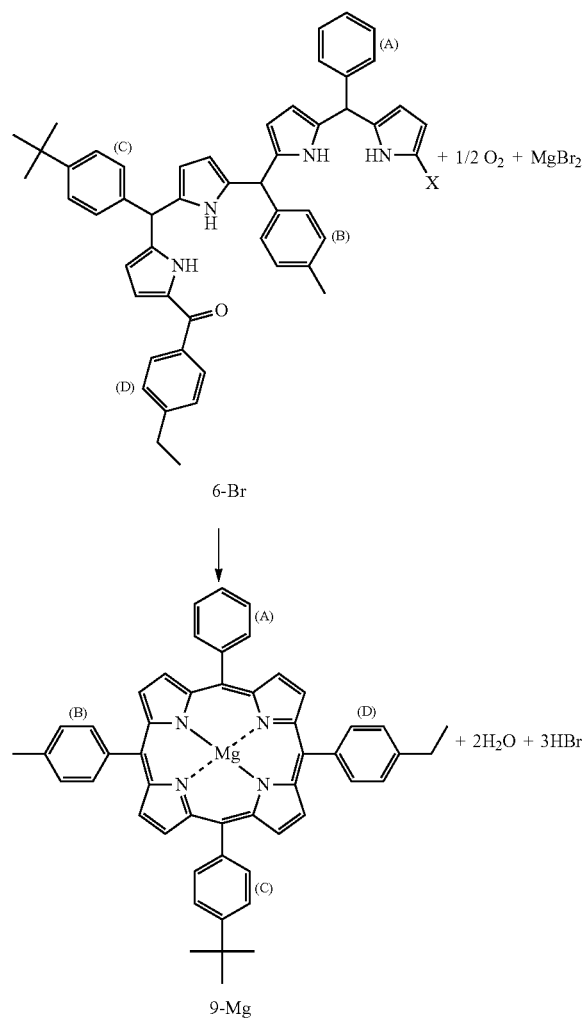

The 2e$^-$/2H$^+$ oxidation of a bilane (6-Br, 6-SEt) during porphyrin formation is presumed to involve oxygen from air. Although the flask that we employed has sufficient headspace to provide a stoichiometric quantity of oxygen (in air) for the oxidation of the intermediate(s), we examined the reaction in the presence of an oxygen atmosphere. The condensation of 6-Br was carried out in toluene containing MgBr$_2$ (3 mol equiv versus 6-Br) and DBU (10 mol equiv versus 6-Br) under reflux with different atmospheric compositions. The reaction with a very slow flow of oxygen afforded 9-Mg in 40% yield, to be compared with 61% yield in the presence of a non-flowing air atmosphere. The reaction under a slow flow of argon gave 9-Mg in 51% yield (Table 5). Under each condition, a trace of free-base porphyrin 9 (0.3-0.8% yield) also was isolated. In summary, providing an excess amount of oxygen in the reaction flask did not improve the yield of the porphyrin. We speculate that excessive oxidation early in the course of reaction may yield species that are less likely to cyclize.

mmol) for 1.5 h. Powdered NaOH (12.0 g, 300 mmol) was added. After stirring for 1 h, the mixture was suction filtered and excess pyrrole was removed under high vacuum. The residue was treated with hexanes (3×100 mL) to facilitate removal of traces of pyrrole. The resulting solid was recrystallized [EtOH/$H_2O$ (6:1)], affording a grayish white solid (21.6 g, 79%): mp 155-157° C.; $^1$H NMR δ 1.31 (s, 9H), 5.45 (s, 1H), 5.94-5.96 (m, 2H), 6.15-6.17 (m, 2H), 6.68-6.70 (m, 2H), 7.13-7.16 (m, 2H), 7.32-7.35 (m, 2H), 7.89-7.95 (br, 2H); $^{13}$C NMR δ 31.5, 34.6, 43.6, 107.2, 108.5, 117.2, 125.7, 128.2, 132.9, 139.1, 149.9; FAB-MS obsd 278.1788, calcd 278.1783 ($C_{19}H_{22}N_2$). Anal. Calcd for $C_{19}H_{22}N_2$: C, 81.97; H, 7.97; N, 10.06. Found: C, 81.82; H, 7.96; N, 10.05. The data ($^1$H NMR, mp, elemental analysis) are consistent with those obtained from samples prepared via earlier routes.[2]

S-2-Pyridyl 4-ethylbenzothioate (2a). Following the general procedure,[18] a solution of 2-mercaptopyridine (11.1 g, 100 mmol) in THF (100 mL) was treated with 4-ethylbenzoylchloride (16.9 g, 100 mmol). The resulting slurry was stirred for 30 min. The precipitate was collected by filtration and washed with hexanes (150 mL) in a Buchner funnel. The filtered material was added into a biphasic solution of saturated aqueous $NaHCO_3$ (100 mL) and diethyl ether (100 mL). The mixture was stirred until the foaming subsided. The organic layer was removed and the water layer was extracted with diethyl ether. The combined organic extract was dried ($Na_2SO_4$), and filtered. The filtrate was concentrated to afford pale yellow solid. The solid was washed with hexanes (~20 mL) to afford a pale yellow solid (20.9 g, 86%): mp 48-50° C.; $^1$H NMR δ 1.27 (t, J=7.6 Hz, 3H), 2.73 (q, J=7.6 Hz, 2H), 7.31-7.35 (m, 3H), 7.72-7.74 (m, 1H), 7.77-7.81 (m, 1H), 7.94-7.96 (m, 2H), 8.67-8.69 (m, 1H); $^{13}$C NMR δ 15.3, 29.1, 123.7, 127.9, 128.5, 131.0, 134.3, 137.3, 150.5, 151.2, 151.6, 189.0; FAB-MS obsd 244.0812, calcd 244.0796 [(M+H)$^+$, M=$C_{14}H_{13}NOS$]. Anal. Calcd for $C_{14}H_{13}NOS$: C, 69.10; H, 5.39; N, 5.76. Found: C, 68.96; H, 5.38; N, 5.70.

5-(4-tert-Butylphenyl)-1-(4-ethylbenzoyl)dipyrromethane (3a). Following a general procedure,[2] a solution of EtMgBr (30 mL, 30.0 mmol, 1.0 M in THF) was added slowly to a solution of 5-(4-tert-butylphenyl)dipyrromethane (1a, 4.17 g, 15.0 mmol) in THF (30 mL) under argon. The resulting mixture was stirred at room temperature for 10 min, and then cooled to −78° C. A solution of S-2-pyridyl 4-ethylbenzothioate (2a, 3.45 g, 15.0 mmol) in THF (30 mL) was added. The solution was stirred at −78° C. for 10 min, then warmed to room temperature. The reaction mixture was quenched by addition of saturated aqueous $NH_4Cl$. The mixture was extracted with ethyl acetate. The organic layer was dried ($Na_2SO_4$) and filtered. The filtrate was concentrated to a minimum amount and silica gel was added. The mixture was then concentrated to dryness. The resulting powder was loaded on the top of the column (5 cm dia×20 cm) eluting with hexanes/$CH_2Cl_2$/ethyl acetate (7:2:1) to afford a light yellow powder (4.06 g, 66%): mp 71-73° C.; $^1$H NMR δ 1.27 (t, J=7.6 Hz, 3H), 1.31 (s, 9H), 2.73 (q, J=7.6 Hz, 2H), 5.50 (s, 1H), 5.99-6.01 (m, 1H), 6.08-6.09 (m, 1H), 6.16-6.18 (m, 1H), 6.70-6.72 (m, 1H), 6.81-6.82 (m, 1H), 7.15 (d, J=8.4 Hz, 2H), 7.28 (d, J=8.4 Hz, 2H), 7.35 (d, J=8.4 Hz, 2H), 7.78 (d, J=8.4 Hz, 2H), 7.93-7.99 (br, 1H), 9.24-9.30 (br, 1H); $^{13}$C NMR δ 15.4, 29.1, 31.5, 34.6, 43.9, 107.8, 108.6, 110.6, 117.8, 120.5, 125.9, 127.9, 128.1, 129.3, 130.9, 131.3, 136.1, 137.8, 141.6, 148.6, 150.3, 184.5; FAB-MS obsd 410.2367, calcd 410.2358 ($C_{28}H_{30}N_2O$). Anal. Calcd for $C_{28}H_{30}N_2O$: C, 81.91; H, 7.37; N, 6.82. Found: C, 82.16; H, 7.49; N, 6.74.

1-(4-Methylbenzoyl)-5-phenyl-9-thiocyanatodipyrromethane (4). Following a general procedure, 5-phenyldipyrromethane (3b, 3.40 g, 10.0 mmol) in $CH_2Cl_2$ (10 mL) was added slowly in a dropwise manner[19] to a stirred solution of ammonium thiocyanate (1.14 g, 15.0 mmol) and iodine (1.27 g, 5.00 mmol) in methanol (10 mL), and the mixture was stirred at room temperature. After 1 h, TLC analysis showed some starting material. Hence, a second portion of a solution of ammoniumthiocyanate (1.14 g, 15.0 mmol) and iodine (1.27 g, 5.00 mmol) in methanol (10 mL) was added dropwise in the reaction mixture, and the reaction mixture was stirred for 2 h. The reaction mixture was concentrated (~10 mL) and was filtered on Buchner funnel. The filtered material was washed with methanol and dried in vacuo to afford a grayish white solid (2.91 g, 73%): mp 183-185° C.; $^1$H NMR δ 2.42 (s, 3H), 5.59 (s, 1H), 6.01-6.03 (m, 1H), 6.11-6.12 (m, 1H), 6.51-6.53 (m, 1H), 6.81-6.83 (m, 1H), 7.15-7.17 (m, 2H), 7.24-7.30 (m, 5H), 7.61-7.63 (m, 2H), 9.34-9.40 (br, 1H), 10.64-10.70 (br, 1H); $^{13}$C NMR δ 21.8, 44.4, 103.1, 110.7, 111.1, 111.2, 120.7, 121.5, 127.8, 128.4, 129.0, 129.3, 129.4, 131.3, 135.5, 138.5, 139.7, 140.7, 142.9, 185.2; FAB-MS obsd 398.1312, calcd 398.1327 ($C_{24}H_{19}N_3OS$); Anal. Calcd for $C_{24}H_{19}N_3OS$: C, 72.52; H, 4.82; N, 10.57. Found: C, 72.28; H, 4.99; N, 10.51.

1-Ethylthio-9-(4-methylbenzoyl)-5-phenyldipyrromethane (5-SEt). Following a general procedure,[20] a solution of EtMgBr (21.0 mL, 21.0 mmol, 1.0 M in THF) in THF (49 mL) cooled at −5° C. was treated slowly with a solution of 1-(4-methylbenzoyl)-5-phenyl-9-thiocyanatodipyrromethane (4, 2.78 g, 7.00 mmol) in THF (35 mL). After stirring at 0° C. for 30 min, TLC showed complete consumption of starting material. The mixture was poured into 20% ice-cold solution of aqueous $NH_4Cl$ (~100 mL) and $Et_2O$ (~100 mL) was added. The organic layer was washed with water, dried and concentrated. Hexanes added. The resulting suspension was filtered on Buchner funnel to afford a pink solid (2.69 g, 96%): mp 179-181° C.; $^1$H NMR δ 1.18 (t, J=7.2 Hz, 3H), 2.42 (s, 3H), 2.60 (q, J=7.2 Hz, 2H), 5.49 (s, 1H), 5.94-5.96 (m, 1H), 6.05-6.06 (m, 1H), 6.30-6.31 (m, 1H), 6.80-6.81 (m, 1H), 7.21-7.36 (m, 7H), 7.75 (d, J=8.0 Hz, 2H), 7.98-8.02 (br, 1H), 9.39-9.43 (br, 1H); $^{13}$C NMR δ 15.3, 21.7, 32.1, 44.5, 109.7, 110.7, 117.2, 119.4, 120.3, 127.7, 128.5, 129.12, 129.18, 129.3, 131.0, 133.8, 135.8, 140.4, 140.7, 142.5, 184.5; FAB-MS obsd 400.1609, calcd 400.1609 ($C_{25}H_{24}N_2OS$); Anal. Calcd for $C_{25}H_{24}N_2OS$: C, 74.97; H, 6.04; N, 6.99. Found: C, 74.83; H, 6.14; N, 6.77.

1-(4-Ethylbenzoyl)-19-ethylsulfanyl-10-(4-methylphenyl)-15-phenyl-5-(4-tert-butylphenyl)bilane (6-SEt). A solution of 5-SEt (0.240 g, 0.600 mmol) in dry THF/methanol (48 mL, 3:1) under argon at room temperature was treated with $NaBH_4$ (0.567 g, 15.0 mmol, 25.0 mol equiv) in small portions with rapid stirring. The progress of the reaction was monitored by TLC analysis [silica, hexanes/ethyl acetate (3:1)]. The reaction completed ~30 min, reaction mixture was poured into a mixture of saturated aqueous $NH_4Cl$ and $CH_2Cl_2$ (250 mL). The organic phase was separated, washed with water and brine, dried ($K_2CO_3$), and concentrated under reduced pressure to yield the carbinol as a yellow-orange foam. The resulting sample was dissolved in anhydrous $CH_2Cl_2$ (24 mL) and treated with 3a (0.246 g, 0.600 mmol). The reaction mixture was stirred for 10 min to achieve complete dissolution of dipyrromethane 3a. 2,6-Di-tert-butylpyridine (175 μL, 0.779 mmol, 32.5 mM) and Sc(OTf)$_3$ (0.0384 g, 0.0779 mmol, 3.25 mM) were added. The progress of the reaction was monitored by TLC analysis [silica, hexanes/ethyl acetate (3:1)]. The reaction mixture was stirred at room temperature for 1 h. A sample of TEA was added (110 μL, 0.779 mmol, 32.5 mM). The reaction mixture changed from red to orange-yellow immediately. The reaction mixture was diluted with $CH_2Cl_2$ (~100 mL), washed with water and brine, dried (Na$_2$SO$_4$) and concentrated to afford an orange paste (drying under high vacuum for 10 min afforded an orange foam). Column chromatography [silica, hexanes/ethyl acetate (3:1)] afforded a yellow foam (0.343 g, 72%): mp 87-95° C.; $^1$H NMR δ 1.15 (t, J=7.1 Hz, 3H), 1.30 (s, 9H), 2.31 (s, 3H), 2.56 (q, J=7.4 Hz, 2H), 2.72 (q, J=7.4 Hz, 2H), 5.26 (s, 1H), 5.32 (s, 1H), 5.38 (s, 1H), 5.69-5.72 (m, 3H), 5.60-5.80 (m, 2H), 6.01-6.03 (m, 1H), 6.23-6.26 (m, 1H), 6.77-6.79 (m, 1H), 7.02-7.15 (m, 8H), 7.26-7.33 (m, 6H), 7.69-7.71 (m, 2H), 7.76-7.78 (m, 4H), 8.00-8.20 (br, 1H), 9.90-10.00 (br, 1H); $^{13}$C NMR δ 14.3, 15.1, 15.4, 21.0, 29.1, 31.3, 32.1, 34.6, 43.9, 44.0, 44.4, 60.5, 107.2, 107.3, 107.4, 107.5, 107.6, 107.8, 108.4, 108.8, 108.9, 110.5, 117.0, 117.9, 120.7, 125.8, 127.1, 128.0, 128.1, 128.3, 128.4, 128.5, 128.7, 129.3, 129.4, 129.5, 130.9, 131.3, 132.1, 133.1, 133.3, 133.4, 135.8, 136.1, 136.6, 138.3, 139.5, 139.6, 142.2, 148.9, 150.3, 171.2, 184.5; $^{15}$N NMR δ-214, -220, -226, $^1$J ($^{15}$N$^1$H) (d, J=120.0 Hz, 1H); The high resolution exact mass spectrum gave m/z 793.3978, which is assigned to the protonated molecule ion of the 2e$^-$/2H$^+$-oxidized derivative of the title compound [calcd 793.3940 for (M'+H)$^+$, M'=C$_{53}$H$_{52}$N$_4$OS, where the title compound has C$_{53}$H$_{54}$N$_4$OS, M=794.40) undergoes 2e$^-$, 2H$^+$ oxidation during the ionization process. LD-MS obsd 794.2, calcd 794.40 (C$_{53}$H$_{54}$N$_4$OS).

1-Bromo-5-phenyl-10-(4-methylphenyl)-15-(4-tert-butylphenyl)-19-(4-ethylbenzoyl)bilane (6-Br) at 25 mM. A sample of 5-Br (0.500 g, 1.20 mmol) in dry THF/methanol (100 mL, 3:1) under argon at room temperature was treated with NaBH$_4$ (1.14 g, 30.0 mmol, 25.0 mol equiv) in small portions with rapid stirring. The progress of the reaction was monitored by TLC analysis [silica, hexanes/ethyl acetate (3:1)]. The reaction was complete in ~30 min. The reaction mixture was poured into a mixture of saturated aqueous NH$_4$Cl and CH$_2$Cl$_2$ (350 mL). The organic phase was separated, washed with water and brine, dried (K$_2$CO$_3$), and concentrated under reduced pressure to yield the carbinol as a yellow-orange foam. The resulting sample was dissolved in anhydrous CH$_2$Cl$_2$ (48.0 mL) and treated with 3a (0.492 g, 1.20 mmol). The reaction mixture was stirred for 10 min to achieve complete dissolution of dipyrromethane 3a. 2,6-Di-tert-butylpyridine (345 μL, 1.56 mmol, 32.5 mM) and Sc(OTf)$_3$ (0.0770 g, 0.156 mmol, 3.25 mM) were added. The progress of the reaction was monitored by TLC analysis [silica, hexanes/ethyl acetate (3:1)]. The reaction mixture was stirred at room temperature for 1 h. A sample of TEA was added (220 μL, 0.0780 mmol, 32.5 mM). The reaction mixture changed from red to orange-yellow immediately. The reaction mixture was diluted with CH$_2$Cl$_2$ (~100 mL), washed with water and brine, dried (Na$_2$SO$_4$) and concentrated to give a brown-yellow paste. Column chromatography [silica, hexanes/ethyl acetate (3:1)] afforded a yellow-orange foam (0.79 g, 80%): mp 95-97° C.; $^1$H NMR in (THF-d$_8$) δ 1.28 (t, J=7.6 Hz, 3H), 1.33 (s, 9H), 2.30 (s, 3H), 2.71 (q, J=7.8 Hz, 2H), 5.29-5.30 (m, 1H), 5.33-5.34 (m, 1H), 5.49-5.51 (m, 1H), 5.57-5.67 (m, 4H), 5.94-5.97 (m, 2H), 6.75-6.76 (m, 1H), 7.06-7.10 (m, 4H), 7.26-7.33 (m, 8H), 7.30-7.34 (m, 4H), 7.81-7.82 (m, 2H), 9.58-9.62 (m, 1H), 9.69-9.72 (brs, 1H), 10.34-10.42 (brs, 1H), 11.04-11.12 (brs, 1H); $^{13}$C NMR δ 14.0, 15.2, 20.1, 20.5, 28.9, 31.1, 34.3, 43.9, 44.2, 44.5, 59.8, 96.4, 106.9, 107.0, 107.1, 109.0, 109.3, 110.0, 119.0, 125.0, 126.4, 127.6, 128.0, 128.4, 128.5, 128.6, 128.7, 129.2, 131.0, 131.8, 131.9, 132.1, 132.2, 132.3, 133.5, 133.6, 133.8, 133.9, 134.0, 135.4, 135.5, 137.1, 139.9, 140.9, 141.1, 142.5, 142.6, 143.3, 147.9, 149.2, 183.1; $^{15}$N NMR δ-214, -220, -226, $^1$J ($^{15}$N$^1$H) (d, J=120.0 Hz, 1H). The high resolution exact mass spectrum gave m/z=811.3035, which is assigned to the protonated molecule ion of the 2e$^-$/2H$^+$-oxidized derivative of the title compound [calcd 811.3011 for (M'+H)$^+$, M'=C$_{51}$H$_{47}$BrN$_4$O, where the title compound has C$_{51}$H$_{49}$BrN$_4$O, M=812.3090) undergoes 2e$^-$, 2H$^+$ oxidation during the ionization process. LD-MS obsd 811.4, calcd 812.3 (C$_{51}$H$_{49}$BrN$_4$O). Anal. Calcd for C$_{51}$H$_{49}$BrN$_4$O: C, 75.26; H, 6.07; N, 6.88. Found: C, 73.19; H, 5.90; N, 6.69. Anal. Comp. is consistent with the structure in the presence of 1 molecule of water.

Synthesis of 6-Br at 500 mM: By following the above procedure, a sample of 5-Br (0.500 g, 1.20 mmol) in dry THF/methanol (100 mL, 3:1) under argon at room temperature was treated with NaBH$_4$ (1.14 g, 30.0 mmol, 25.0 mol equiv) in small portions with rapid stirring. The progress of the reaction was monitored by TLC analysis [silica, hexanes/ethyl acetate (3:1)]. The reaction was complete in ~30 min. The reaction mixture was poured into a mixture of saturated aqueous NH$_4$Cl and CH$_2$Cl$_2$ (250 mL). The organic phase was separated, washed with water and brine, dried (K$_2$CO$_3$), and concentrated under reduced pressure to yield the carbinol as a yellow-orange foam. The resulting sample was dissolved in anhydrous CH$_2$Cl$_2$ (2.4 mL) and treated with 3a (0.492 g, 1.20 mmol). The reaction mixture was stirred for 10 min to achieve complete dissolution of dipyrromethane 3a. 2,6-Di-tert-butylpyridine (17.0 μL, 0.0780 mmol, 32.5 mM) and Sc(OTf)$_3$ (0.00380 g, 0.00780 mmol, 3.25 mM) were added. The progress of the reaction was monitored by TLC analysis [silica, hexanes/ethyl acetate (3:1)]. The reaction mixture was stirred at room temperature for 1 h. A sample of TEA was added (10.0 μL, 0.0780 mmol, 32.5 mM). The reaction mixture changed immediately from red to orange-yellow. The reaction mixture was diluted with CH$_2$Cl$_2$ (~100 mL), washed with water and brine, dried (Na$_2$SO$_4$) and concentrated to give a brown-yellow paste. Column chromatography [silica, hexanes/ethyl acetate (3:1)] afforded a yellow-orange foam (0.34 g, 35%). The data ($^1$H NMR, $^{13}$C NMR, LD-MS, FAB-MS, and mp) were consistent with those obtained from samples prepared via earlier routes.

20-[9-Borabicyclo[3.3.1]non-9-yl]-19-bromo-1-(4-ethylbenzoyl)-10-(4-methylphenyl)-15-phenyl-5-(4-t-butylphenyl)bilane (6-Br-9-BBN). By following the reported procedure for 1-acyldipyrromethanes,[17] a solution of 6-Br (0.41 g, 0.50 mmol) in toluene (1 mL) was treated with TEA (170 μL, 1.20 mmol) followed by 9-BBN-OTf (2 mL, 1 mmol, 0.5 M in hexanes). The reaction was complete in ~30 min. The mixture was passed through an alumina column eluting with CH$_2$Cl$_2$. The product was eluted as fast-moving yellow band, which upon concentration afforded a yellow solid (0.38 g, 80%): mp 103-105° C.; $^1$H NMR δ 0.562-0.62 (brs, 1H), 0.72-0.787 (brs, 1H), 1.25-1.31 (brs, 12H), 1.61-1.96 (m, 8H), 1.95-2.10 (m, 2H), 2.17-2.23 (m, 2H), 2.31 (s, 3H), 2.76 (q, J=7.4 Hz, 2H), 5.27-5.30 (m, 4H), 5.70-5.75 (m, 4H), 5.86-5.87 (m, 1H), 6.02-6.04 (m, 1H), 6.33-6.34 (m, 1H), 7.01-7.03 (m, 2H), 7.07-7.09 (m, 4H), 7.14-7.19 (m, 2H), 7.24-7.29 (m, 8H), 7.37-7.39 (m, 2H), 7.53-7.54 (brs, 1H), 7.64-7.82 (brs, 1H), 7.76-7.84 (brs, 1H), 8.12-8.14 (brs, 2H); $^{13}$C NMR δ 15.5, 21.3, 24.0, 25.2, 26.1, 26.4, 29.4, 30.3, 31.3, 31.4, 31.6, 34.6, 34.7, 34.8, 43.9, 44.4, 44.5, 53.7, 97.1, 107.4, 107.5, 107.8, 107.9, 108.2, 109.3, 110.7, 118.3, 120.8, 125.6, 127.3, 128.1, 128.4, 128.5, 128.53, 128.6, 128.8, 128.9, 129.4, 129.44, 130.0, 131.4, 131.5, 131.8, 131.9, 132.43, 132.44, 133.1, 133.2, 134.2, 134.8, 136.67, 136.70, 139.2, 139.4, 141.6, 149.9, 151.2, 152.5, 174.3; The high resolution exact mass spectrum gave m/z=932.4196, which is assigned to the protonated molecule ion of (i) —CH$_3$ (a methyl unit undergoes cleavage) (ii) the 2e$^-$/2H$^+$-oxidized derivative of the title compound [calcd 932.4200 for (M'+H)$^+$, M'=C$_{59}$H$_{61}$BBrN$_4$O, where the title compound has C$_{60}$H$_{65}$BBrN$_4$O, M=947.44) undergoes (1) a methyl unit cleavage (2) 2e$^-$, 2H$^+$ oxidation during the ionization process. LD-MS obsd 934.3, calcd 947.47 (C$_{60}$H$_{65}$ BBrN$_4$O). Anal. Calcd for C$_6$H$_{65}$BBrN$_4$O: C, 75.95; H, 6.90; N, 5.90. Found: C, 76.33; H, 7.17; N, 5.78.

Studies of the Stepwise Synthesis and Intermediates:

Oxidation and Metalation of 1-(4-Ethylbenzoyl)-19-ethylsulfanyl-15-phenyl-10-(4-methylphenyl)-5-(4-tert-butylphenyl)bilane (6-SEt), illustrated for Zn(OAc)$_2$ Giving 7-Zn. A solution of bilane 6-SEt (0.0900 g, 0.113 mmol) in THF (2.20 mL, 52.0 mM) was treated with DDQ (0.0560 g, 0.247 mmol, 2.20 mol equiv) under vigorous stirring. The reaction mixture changed from yellow to dark green. Zn(OAc)$_2$ (0.0620 g, 0.340 mmol, 3.00 mol equiv) was added. The reaction mixture darkened. TLC analysis [silica, hexanes/CH$_2$Cl$_2$ (5:3)] showed the reaction was completed in ~30 min, whereupon water was added (~20 mL). The resulting mixture was extracted with CH$_2$Cl$_2$. The extract was washed with water and brine, dried (Na$_2$SO$_4$) and concentrated to give a dark green-purple solid. Methanol (~10 mL) was added, and the resulting suspension was placed in a sonication bath for a few minutes followed by centrifugation. The methanol layer was decanted leaving behind a dark green-purple solid (0.029 g, 30%): mp 92-95° C.; $^1$H NMR δ 1.36 (s, 9H), 2.24 (s, 3H), 2.63 (q, J=7.1 Hz, 2H), 3.04 (q, J=7.1 Hz, 2H), 5.74-5.75 (m, 1H), 6.11-6.13 (m, 1H), 6.22-6.24 (m, 1H), 6.33 (s, 2H), 6.46-6.48 (m, 1H), 6.75 (s, 2H), 6.82-6.83 (m, 1H), 6.91-6.93 (m, 1H), 6.97-7.00 (m, 2H), 7.26-7.29 (m, 11H), 7.36 (s, 1H), 7.49-7.51 (m, 2H); $^{13}$C NMR δ 15.1, 16.4, 21.9, 28.4, 29.1, 29.9, 31.6, 34.9, 80.0, 115.5, 115.9, 123.8, 123.9, 124.0, 124.4, 125.4, 126.6, 127.0, 127.1, 127.7, 127.9, 129.1, 130.5, 130.6, 130.8, 130.9, 131.1, 131.4, 132.7, 135.7, 135.9, 136.3, 136.4, 138.1, 139.1, 141.1, 142.3, 143.2, 144.0, 145.0, 145.1, 147.0, 148.0, 151.5, 155.5, 165.1, 178.6, 190.7; LD-MS obsd 852.7; calcd 852.3; λ$_{abs}$ 479 nm (C$_{53}$H$_{48}$N$_4$OSZn).

Desulfurization of 7-Zn to Give Biladiene-Metal Complex 8-Zn. A sample of 7-Zn (0.005 g, 0.006 mmol) was placed in a microscale reaction vial. Following the reported procedure for desulfurizing 1,9-bis(alkylthio)dipyrromethanes,$^3$ a solid portion of wet Raney nickel (1 g) was removed from a Raneynickel—water slurry by a spatula and washed with THF (~10 mL) three times. The washed Raney nickel was transferred to the reaction vial with 0.5 mL THF. The reaction mixture changed from green-purple to dark red. The progress of the reaction was monitored by TLC analysis [silica, hexanes/ethyl acetate (8:3)] and LD-MS. The reaction was complete in 1 h. The residue was filtered through a sintered glass funnel and the filtered material was washed with THF (~20 mL). The filtrate was concentrated to afford a dark red paste (0.015 g): LD-MS obsd 791.8 calcd 792.3 (C$_{51}$H$_{44}$N$_4$OZn).

Zn-Biladiene-Carbinol (8-Zn—OH). A Crude Sample (0.015 g) of 7-Zn from the previous step was placed in a microscale reaction vial, sealed with a rubber septum and flooded with argon for 5 min. The sample was dissolved in dry THF/methanol (1.5 mL, 4:1) at room temperature The septum was removed to add NaBH$_4$ (0.0110 g, 0.300 mmol, 50.0 mol equiv) in one batch. The reaction was checked with LD-MS. The starting material was consumed in ~40 min. The reaction mixture was poured into a mixture of saturated aqueous NH$_4$Cl and CH$_2$Cl$_2$ (50 mL). The organic phase was separated, washed with water and brine, dried (K$_2$CO$_3$) and concentrated under reduced pressure to yield a dark red paste (0.025 g), which was dried under high vacuum for 10 min: LD-MS obsd 794.5, calcd 794.3 (C$_{51}$H$_{46}$N$_4$OZ$_n$).

ABCD-porphyrin Formation (9). The sample of 8-Zn—OH (0.025 g) was dissolved in anhydrous CH$_2$Cl$_2$ (0.5 mL, 12 mM) at room temperature in a microscale reaction vial, which was fitted with a vented septum and flooded with argon. A sample of 2,6-di-tert-butylpyridine (4.00 μL, 0.0160 mmol, 32.5 mM) was added dropwise into the reaction vial. Sc(OTf)$_3$ (0.001 g, 0.002 mmol, 4 mM) was added. The reaction mixture darkened immediately. The progress of the reaction was monitored by absorption spectroscopy of oxidized reaction aliquots (1 μL aliquot is placed into 3 mL of CH$_2$Cl$_2$, to which 1 drop of 10 mM DDQ in toluene is added prior to absorption spectroscopy in CH$_2$Cl$_2$). The intermediate (biladiene-ac zinc complex, 476 nm) disappeared after ~40 min, whereupon DDQ (0.003 g, 0.01 mmol) was added. The reaction mixture was stirred for an additional 20 min. A sample of TEA (3.0 μL, 0.020 mmol) was added. The crude reaction mixture was diluted with CH$_2$Cl$_2$ (20 mL) and poured into water. The organic phase was separated and the water layer was extracted with CH$_2$Cl$_2$. The combined organic extract was washed with water and brine, dried (Na$_2$SO$_4$) and concentrated. Filtration through a pad of alumina (CH$_2$Cl$_2$) afforded porphyrin (2%, spectroscopic yield): LD-MS obsd 712.8, calcd 712.4 (C$_{51}$H$_{44}$N$_4$); λ$_{abs}$ 418, 463, 472, 485, 518 nm.

General Procedure for Stepwise ABCD-Porphyrin Synthesis (without Full Characterization of Intermediates).

A. Example with MgI$_2$:

(Step 1) Oxidation and Metalation (7-Mg). A solution of bilane 6-SEt (0.050 g, 0.063 mmol) in THF (1.25 mL, 50.0 mM) was treated with DDQ (0.050 g, 0.22 mmol, 3.5 mol equiv) under vigorous stirring. The reaction mixture changed from yellow to dark green immediately. After 10 min, MgI$_2$ (0.053 g, 0.19 mmol, 3.0 mol equiv) was added. The reaction mixture darkened. TLC analysis [silica, hexanes/ethyl acetate (3:1)] revealed consumption of starting material after ~30 min, whereupon TEA (265 μL, 1.89 mmol) was added. Water (~20 mL) added and the resulting mixture was extracted with CH$_2$Cl$_2$. The extract was washed with water and brine, dried (Na$_2$SO$_4$) and concentrated. The crude product was dried under high vacuum for 10 min affording a dark green paste (0.068 g): LD-MS obsd 811.6; calcd 812.3 (C$_{53}$H$_{48}$MgN$_4$OS); λ$_{abs}$ 440 nm (broad).

(Step 2) Desulfurization (8-Mg). Following a reported procedure,$^3$ a solid portion of wet Raney nickel (4 g) was removed from a Raney-nickel-water slurry by a spatula and washed with THF (~10 mL) five times. The washed Raney nickel was transferred to the reaction flask by pipette (THF 2.5 mL) under vigorous stirring. The reaction mixture changed from dark green to dark red. On the basis of TLC analysis (silica, CH$_2$Cl$_2$) and LD-MS, the reaction was complete in 1 h. The mixture was filtered through a sintered glass funnel. The filtered material was washed with THF (~100 mL), concentrated and dried under high vacuum affording a dark red paste: LD-MS obsd 753.4, calcd 752.3 (C$_{51}$H$_{44}$MgN$_4$O).

(Step 3) Reduction (8-Mg—OH). A solution of 7-Mg in dry THF/methanol (5 mL, 3:1) under argon at room temperature was treated with NaBH$_4$ (0.0600 g, 1.58 mmol, 25.0 mol equiv) in one batch. The progress of the reaction was checked with LD-MS. The starting material was consumed in ~40 min. The reaction mixture poured into a mixture of saturated aqueous NH$_4$Cl and CH$_2$Cl$_2$ (50 mL). The organic phase was separated, washed with water and brine, dried (K$_2$CO$_3$) and concentrated under reduced pressure. The resulting product was dried under high vacuum for 10 min affording a dark red paste (0.035 g): LD-MS obsd 735.7, calcd 736.4 (C$_{51}$H$_{46}$MgN$_4$).

(Step 4) Condensation and Oxidation (9). A solution of 8-Mg—OH in anhydrous CH$_2$Cl$_2$ (2.50 mL, 12.5 mM) under argon was treated with a sample of 2,6-di-tert-butylpyridine (18.0 µL, 0.0810 mmol, 32.5 mM). The reaction mixture was stirred for 5 min and then Sc(OTf)$_3$ (0.004 g, 0.008 mmol, 3.25 mM) was added. The reaction mixture darkened immediately. The reaction was monitored with absorption spectroscopy. Three bands (319, 446, 501 nm) were observed. A sample of TEA (22.0 µL, 0.0810 mmol) was added. The reaction was checked by absorption spectroscopy and a strong band was observed at 419 nm. The reaction mixture was diluted with CH$_2$Cl$_2$ (30 mL) and poured into water. The organic phase was separated washed with water, and brine, dried (Na$_2$SO$_4$) and concentrated affording a dark brown-black paste. The crude reaction mixture was filtered through a column (silica, CH$_2$Cl$_2$). The resulting porphyrin-containing fraction was concentrated. Methanol was added, and the resulting suspension was placed in sonication bath for few minutes followed by centrifugation. Methanol was decanted affording a purple solid (13 mg, 27%): $^1$H NMR δ −2.77 (brs, 2H), 1.54 (m, 3H), 1.61 (s, 9H), 2.70 (s, 3H), 3.00 (q, J=7.6 Hz, 2H), 7.00 (d, J=8.2, 2H), 7.24 (d, J=8.8, 3H), 7.74-7.77 (m, 4H), 8.10-8.15 (m, 5H), 8.21-8.23 (m, 2H), 8.82-8.88 (m, 8H); $^{13}$C NMR δ 15.9, 21.7, 29.1, 31.2, 31.9, 35.1, 121.7, 122.0, 122.2, 123.8, 126.4, 127.0, 127.6, 127.9, 131.0, 131.1, 131.2, 131.3, 134.2, 134.3, 134.4, 134.5, 137.6, 139.0, 139.1, 139.3, 141.7, 141.9, 142.1, 143.9, 150.8; LD-MS obsd 712.8, FAB-MS obsd 712.3575, calcd 712.3566 (C$_{51}$H$_{44}$N$_4$); λ$_{abs}$ 419, 516, 551, 592, 649 nm.

B. Example with Pd(OAc)$_2$:

(Step 1) Oxidation and Metalation (7-Pd). A solution of bilane 6-SEt (0.050 g, 0.063 mmol) in THF (1.25 mL, 50.0 mM) was treated with DDQ (0.0500 g, 0.221 mmol, 3.50 mol equiv) under vigorous stirring. The reaction mixture changed from yellow to dark green immediately. Pd(OAc)$_2$ (0.0430 g, 0.189 mmol, 3.00 mol equiv) was added. The reaction mixture darkened. The reaction mixture was checked by TLC analysis [silica, CH$_2$Cl$_2$/ethyl acetate (1:1)]. The reaction was completed in 20 min, whereupon TEA (265 µL, 1.89 mmol) was added. The reaction mixture was treated with water (~20 mL) and the resulting mixture was extracted with CH$_2$Cl$_2$. The extract was washed with brine, dried (Na$_2$SO$_4$) and concentrated affording a brown paste: LD-MS obsd 894.0; calcd 894.3 (C$_{53}$H$_{48}$N$_4$OPdS); λ$_{abs}$ 347, 445 nm (broad).

(Steps 2-4) Desulfurization Plus All Other Steps (9-Pd). A solution of the 7-Pd in THF (2.5 mL, 25 mM) treated with a solid portion of wet Raney nickel (4 g), removed from a Raney-nickel-water slurry by a spatula and washed with THF (~10 mL) five times. Washed Raney nickel was transferred to the reaction flask by pipette (THF 2.5 mL) under vigorous stirring. The reaction mixture changed from dark brown to dark red. The progress of the reaction was monitored by TLC analysis [silica, CH$_2$Cl$_2$]. Starting material was consumed ~30 min affording palladium porphyrin. The mixture was filtered through a sintered glass funnel to remove the Raney nickel. The filtered material was washed with THF (~100 mL). The filtrate was concentrated affording a dark red orange paste. The crude reaction mixture was filtered through a column (silica, CH$_2$Cl$_2$). The resulting porphyrin-containing fraction was concentrated. Methanol was added, and the resulting suspension was placed in sonication bath for few minutes followed by centrifugation. Methanol was decanted affording a purple solid (25 mg, 49% on the basis the amount of 6-SEt employed in Step 1): $^1$H NMR δ 1.60 (s, 9H), 2.70 (s, 3H), 3.00 (q, J=7.6 Hz, 2H), 7.52-7.57 (m, 5H), 7.71-7.76 (m, 6H), 8.03-8.10 (m, 7H), 8.16-8.18 (m, 2H), 8.78-8.83 (m, 2H), 8.84-8.85 (m, 6H); $^{13}$C NMR δ 15.9, 21.7, 29.1, 31.2, 31.9, 35.1, 121.7, 122.0, 122.2, 123.8, 126.4, 127.0, 127.6, 127.9, 131.0, 131.1, 131.2, 131.3, 134.2, 134.3, 134.4, 134.5, 137.6, 139.0, 139.1, 139.3, 141.7, 141.9, 142.1, 143.9, 150.8; LD-MS obsd 816.3, FAB-MS 816.2616 calcd 816.2577 (C$_{51}$H$_{42}$N$_4$Pd); λ$_{abs}$ 416, 523 nm.

One-Flask ABCD-Metalloporphyrin Synthesis from Bilanes.

Protocol for Table 1: Palladium-Mediated Cyclization of Bilane 6-SEt (25 mM). A sample of bilane 6-SEt (0.010 g, 0.013 mmol), KOH (0.0040 g, 0.063 mmol) and Pd(CH$_3$CN)$_2$Cl$_2$ (0.0030 g, 0.013 mmol) were placed in a 2 mL microscale reaction vial sealed with a rubber septum. Ethanol (0.520 mL) was added and a needle was placed through septum. The heterogeneous reaction mixture was stirred and heated at 75° C. for 2 h. The progress of the reaction was monitored by TLC analysis (silica, CH$_2$Cl$_2$). The reaction completed in ~2 h. The residue was concentrated. The resulting crude product was dissolved in CH$_2$Cl$_2$ and passed through a pad of alumina (CH$_2$Cl$_2$). The resulting porphyrin-containing fraction was concentrated. Methanol was added, and the resulting suspension was placed in a sonication bath for a few minutes followed by centrifugation. Methanol was decanted affording a red-orange solid (spectroscopic yield 38%): $^1$H NMR δ 1.53 (t, J=7.6 Hz, 3H), 1.60 (s, 9H), 2.70 (s, 3H), 3.00 (q, J=7.6 Hz, 2H), 7.52-7.57 (m, 5H), 7.71-7.76 (m, 6H), 8.03-8.10 (m, 7H), 8.16-8.18 (m, 2H), 8.78-8.83 (m, 2H), 8.84-8.85 (m, 6H); $^{13}$C NMR δ 15.9, 21.7, 29.1, 31.2, 31.9, 35.1, 121.7, 122.0, 122.2, 123.8, 126.4, 127.0, 127.6, 127.9, 131.0, 131.1, 131.2, 131.3, 134.2, 134.3, 134.4, 134.5, 137.6, 139.0, 139.1, 139.3, 141.7, 141.9, 142.1, 143.9, 150.8; LD-MS obsd 816.1, FAB-MS obsd 816.272 calcd 816.240 (C$_{51}$H$_{42}$N$_4$Pd); λ$_{abs}$ 417, 524 nm.

Note: in each of the following reactions wherein a zinc or magnesium porphyrin was prepared, a trace amount of free base porphyrin was typically formed (yield <1%). In several cases, the quantity of free base porphyrin has been determined by isolation. More rigorous quantitation in each case will be performed upon repetition of the following procedures.

Protocol for Table 2: NiCl$_2$ with Bilane 6-SEt (100 mM). A sample of bilane 6-SEt (0.010 g, 0.013 mmol), KOH (0.0040 g, 0.065 mmol) and NiCl$_2$ (0.0030 g, 0.026 mmol) were placed in 2 mL microscale reaction vial sealed with rubber septum. Ethanol (0.5 mL) added and a needle was placed through septum. The reaction vial was sonicated and the heterogeneous reaction mixture heated overnight at 70° C. The progress of the reaction was monitored by TLC analysis (silica, CH$_2$Cl$_2$). After the reaction was complete (~12 h) the solvent was evaporated. The residue was dissolved in CH$_2$Cl$_2$ and passed through a column (silica, CH$_2$Cl$_2$). The resulting porphyrin-containing fractions were concentrated to give an orange solid. Methanol was added, and the resulting suspension was placed in sonication bath for few minutes followed by centrifugation. Methanol was decanted affording an orange solid (12% spectroscopic yield): $^1$H NMR δ 1.53 (t, J=8.4 Hz, 3H), 1.62 (s, 9H), 2.64 (s, 3H), 2.94 (q, J=8.4 Hz, 2H), 7.46-7.52 (m, 4H), 7.66-7.70 (m, 4H), 7.88-7.94 (m, 4H), 8.00-8.01 (m, 2H), 8.72-8.74 (m, 2H), 8.75-8.76 (m, 4H); LD-MS obsd 768.6, FAB-MS obsd 768.2761, calcd 768.2763 (C$_{51}$H$_{42}$NiN$_4$); λ$_{abs}$ 415, 528 nm.

Protocol for Table 4: (i) Microscale Synthesis Procedure, Exemplified for 9-Mg. A solution of 6-Br (0.050 g, 0.062 mmol) in dry toluene at room temperature (0.62 mL) in a 1 mL microscale reaction vial (fitted with a vented teflon septum) was treated with DBU (0.094 mL, 0.62 mmol, 10 mol equiv versus 6-Br). The reaction mixture darkened, and MgBr$_2$ (0.034 g, 0.19 mmol, 3 mol equiv versus bilane 6-Br) was added. The heterogeneous reaction mixture was sonicated for 1 min and stirred under open-air reflux. On the basis of TLC analysis (silica, CH$_2$Cl$_2$) and absorption spectroscopy of samples from the crude reaction mixture, porphyrin formation was complete in 1.5 h. The crude reaction mixture was filtered through a column (alumina 40 g, 2.5 cm dia×10 cm, $CH_2Cl_2 \rightarrow CH_2Cl_2$/ethyl acetate 5:3→1:1, ~250 mL of solvent was used). The porphyrin-containing fraction was concentrated to give a purple solid (0.032 g, 69%). The characterization data ($^1$H NMR, $^{13}$C NMR, LD-MS and absorption spectrum) were consistent with those obtained from samples of 9-Mg prepared via earlier routes.

Protocol for Table 4: (ii) Microscale Synthesis Procedure, Exemplified for 9-Zn. Following the standard procedure, a solution of bilane 6-Br (0.050 g, 0.062 mmol) in dry toluene (0.620 mL) was treated with DBU (0.090 mL, 0.62 mmol, 10 mol equiv versus 6-Br). The reaction mixture darkened and $Zn(OAc)_2$ (0.035 g, 0.19 mmol, 3 mol equiv) was added. The reaction mixture was stirred under open-air reflux. The crude reaction mixture was checked by absorption spectroscopy. The formation of metalloporphyrin was complete in 1 h. The crude reaction mixture was concentrated and filtered through a column (silica, $CH_2Cl_2$). Porphyrin-containing fractions were concentrated to afford a purple solid (24 mg, 50%): $^1$H NMR δ 1.54 (t, J=7.6 Hz, 3H), 1.62 (s, 9H), 2.71 (s, 3H), 3.00 (q, J=7.8 Hz, 2H), 7.54-7.56 (m, 4H), 7.74-7.77 (m, 5H), 8.01-8.16 (m, 6H), 8.16-8.18 (m, 2H), 8.78-8.83 (m, 4H), 8.84-8.85 (m, 4H); $^{13}$C NMR δ 16.0, 21.8, 29.1, 30.0, 32.0, 32.1, 35.1, 121.5, 121.8, 121.9, 122.0, 123.4, 126.0, 126.5, 127.2, 131.8, 131.9, 132.0, 132.1, 134.8, 134.91, 134.94, 135.0, 136.7, 141.0, 141.1, 141.2, 143.1, 144.1, 149.96, 150.0, 150.25, 150.28; LD-MS obsd 774.9, FAB-MS obsd 774.2698, calcd 774.2701 ($C_{51}H_{42}N_4Zn$); $\lambda_{abs}$ 420, 548, 616 nm.

Protocol for Table 5: Examination of Effects of Atmosphere on Porphyrin Formation. A sample of 6-Br (0.0200 g, 0.0246 mmol) was placed in an oven-dried round bottom flask (5 mL). The flask was sealed with a teflon septum and dry toluene was added at room temperature (0.250 mL). The mixture was stirred at room temperature for 1 min and DBU (0.0380 mL, 0.246 mmol, 10.0 mol equiv versus 6-Br) was added. The reaction mixture was stirred for 5 min, reaction mixture darkened, and $MgBr_2$ (0.0140 g, 0.0738 mmol, 3.00 mol equiv versus bilane 6-Br) was added. The heterogeneous reaction mixture was sonicated for a few secs, and then stirred at room temperature for 1 min. The reaction mixture was stirred under very slow oxygen flow at reflux (oil bath temperature 135° C.) for 3 h. TLC analysis (silica, $CH_2Cl_2$) and absorption spectroscopy of sample removed from the crude reaction mixture, revealed the formation of magnesium porphyrin and an intermediate which is more polar than the porphyrin and possessing a broad band at 468 nm. The crude reaction mixture did not reveal any change even after 8 h under reflux with slow oxygen flow. The crude reaction mixture was concentrated and filtered through a column (alumina 280 g, 4 cm dia×15 cm, $CH_2Cl_2 \rightarrow CH_2Cl_2$/ethyl acetate 5:3→1:1, 600 mL). A trace amount of free base porphyrin 9 eluted near the solvent front ($CH_2Cl_2$) and was obtained in 0.8% spectroscopic yield. The dominant porphyrin-containing fraction eluted later ($CH_2Cl_2$/ethyl acetate) and was concentrated to give a purple solid (7 mg, 40% isolated yield, 31% spectroscopic yield). The characterization data ($^1$H NMR, $^{13}$C NMR, LD-MS and absorption spectrum) were consistent with those obtained from samples of 9-Mg prepared via earlier routes. Data for free base porphyrin 9: LD-MS obsd 712.9, calcd 712.3566 ($C_{51}H_{44}N_4$); $\lambda_{abs}$ 419, 516, 551, 592, 649 nm.

Preparative Protocols (i) Large-Scale Synthesis (9-Mg). A solution of 6-Br (0.500 g, 0.620 mmol) in dry toluene at room temperature (6.2 mL) in a 25 mL round-bottom flask (fitted with a vented teflon septum) was treated with DBU (0.940 mL, 6.20 mmol, 10.0 mol equiv versus 6-Br). The reaction mixture darkened, and $MgBr_2$ (0.340 g, 1.86 mmol, 3 mol equiv versus bilane 6-Br) was added. The heterogeneous reaction mixture was sonicated for 1 min and stirred under open-air reflux. On the basis of TLC analysis (silica, $CH_2Cl_2$) and absorption spectroscopy of samples removed from the crude reaction mixture, porphyrin formation was complete in 2 h. The crude reaction mixture was filtered through a column (alumina 480 g, 4 cm dia×30 cm, $CH_2Cl_2 \rightarrow CH_2Cl_2$/ethyl acetate 5:3→1:1, ~1.5 L of solvent was used). The porphyrin-containing fraction was concentrated to give a purple solid (0.295 g, 65%): $^1$H NMR δ 1.55 (t, J=7.8 Hz, 3H), 1.62 (s, 9H), 2.71 (s, 3H), 3.00 (q, J=7.8 Hz, 2H), 7.52-7.57 (m, 4H), 7.72-7.74 (m, 5H), 8.10-8.14 (m, 6H), 8.21-8.230 (m, 2H), 8.84-8.89 (m, 8H); $^{13}$C NMR δ 16.0, 21.8, 29.1, 30.0, 32.0, 32.1, 35.1, 121.5, 121.8, 121.9, 122.0, 123.4, 126.0, 126.5, 127.2, 131.9, 132.0, 132.05, 132.08, 132.12, 134.7, 134.9, 134.91, 135.0, 136.8, 140.9, 141.0, 141.2, 143.1, 144.0, 150.0, 150.21, 150.25, 150.28; LD-MS obsd 734.7; FAB-MS obsd 734.3257, calcd 734.3260 ($C_{51}H_{42}MgN_4$); $\lambda_{abs}$ 406, 426, 565, 605 nm.

(ii) Solventless Reaction (9-Mg). A sample of 6-Br (0.0500 g, 0.0615 mmol) was placed in an oven-dried flask (5 mL). DBU (0.0900 mL, 0.615 mmol, 10.0 mol equiv versus 6-Br) was added. The reaction mixture was stirred for 5 min, whereupon the reaction mixture darkened. $MgBr_2$ (0.0340 g, 0.186 mmol, 3.00 mol equiv versus bilane 6-Br) was added. The heterogeneous reaction mixture was sonicated for a few secs, and then stirred at room temperature for 1 min. The reaction mixture was heated (oil bath temperature 135° C.) for 1 h. TLC analysis (silica, $CH_2Cl_2$) and absorption spectroscopy of a sample removed from the crude reaction mixture revealed formation of the magnesium porphyrin and two, more polar products (a green spot and a red spot). On the basis of TLC analysis, no change was observed even the reaction mixture was stirred for 4 h. The crude reaction mixture was concentrated and filtered through a column (alumina 280 g, 4 cm dia×15 cm, $CH_2Cl_2 \rightarrow CH_2Cl_2$/ethyl acetate 5:3→1:1). A trace amount of free base porphyrin 9 eluted near the solvent front ($CH_2Cl_2$) and was obtained in 1% spectroscopic yield. The dominant porphyrin-containing fraction eluted later ($CH_2Cl_2$/ethyl acetate) and was concentrated to give a purple solid (16.0 mg, 35%). The characterization data ($^1$H NMR, $^{13}$C NMR, LD-MS and absorption spectrum) were consistent with those obtained from samples of 9-Mg prepared via earlier routes. Data for free base porphyrin 9: LD-MS obsd 712.8, calcd 712.3566 ($C_{51}H_{44}N_4$); $\lambda_{abs}$ 419, 516, 551, 592, 649 nm.

(iii) Large-Scale Synthesis of 9-Zn: A solution of 6-Br (0.270 g, 0.332 mmol) in dry toluene at room temperature (3.0 mL) in a 25 mL oven dried round-bottom flask (fitted with a vented teflon septum) was treated with DBU (0.500 mL, 3.32 mmol, 10.00 mol equiv versus 6-Br). The reaction mixture darkened, and $Zn(OAc)_2$ (0.183 g, 0.996 mmol, 3.00 mol equiv versus bilane 6-Br) was added. The heterogeneous reaction mixture was sonicated for a few secs. The reaction mixture was stirred at room temperature for 1 min. The heterogeneous reaction mixture was stirred under open-air reflux (oil bath temperature 135° C.). On the basis of TLC analysis (silica, $CH_2Cl_2$) and absorption spectroscopy of samples removed from the crude reaction mixture, porphyrin formation was complete in 3 h. The crude reaction mixture was filtered through a column (silica, 185 g, 4 cm dia×40 cm, $CH_2Cl_2$, ~2.0 L of solvent was used). The porphyrin-containing fraction was concentrated to give a purple solid (0.060 g, 23%). A trace amount of free base porphyrin 9 (0.5% spectroscopic yield) eluted after the dominant porphyrin-containing fraction: $^1$H NMR δ 1.54 (t, J=7.6 Hz, 3H), 1.62 (s, 9H), 2.71 (s, 3H), 3.00 (q, J=7.8 Hz, 2H), 7.54-7.56 (m, 4H), 7.74-7.77 (m, 5H), 8.01-8.16 (m, 6H), 8.16-8.18 (m, 2H), 8.78-8.83 (m, 3H), 8.84-8.85 (m, 4H); $^{13}$C NMR δ 16.0, 21.8, 29.1, 30.0, 32.0, 32.1, 35.1, 121.5, 121.8, 121.9, 122.0, 123.4, 126.0, 126.5, 127.2, 131.8, 131.9, 132.0, 132.1, 134.8, 134.91, 134.94, 135.0, 136.7, 141.0, 141.1, 141.2, 143.1, 144.1, 149.96, 150.0, 150.25, 150.28; LD-MS obsd 774.9, FAB-MS obsd 774.2698, calcd 774.2701 ($C_{51}H_{42}N_4Zn$); $\lambda_{abs}$ 420, 548, 616 nm. Data for 9: LD-MS obsd 712.9, calcd 712.3566 ($C_{51}H_{44}N_4$); $\lambda_{abs}$ 419, 516, 551, 592, 649 nm. This procedure is to be repeated at larger scale with less chromatographic solvent where the free base porphyrin will not be isolated.

REFERENCES (1) Zaidi, S. H. H.; Fico, R. M., Jr.; Lindsey, J. S. *Org. Process Res. Dev.* 2006, 10, 118-134.
(2) Rao, P. D.; Littler, B. J.; Geier, G. R., III; Lindsey, J. S. *J. Org. Chem.* 2000, 65, 1084-1092.
(3) Thamyongkit, P.; Bhise, A. D.; Taniguchi, M.; Lindsey, J. S. *J. Org. Chem.* 2006, 71, 903-910.
(4) Harris, R. L. N.; Johnson, A. W.; Kay, I. T. *J. Chem. Soc. C* 1966, 22-29.
(5) Sharada, D. S.; Muresan A. Z.; Muthukumaran, K.; Lindsey, J. S. *J. Org. Chem.* 2005, 70, 3500-3510.
(6) Diaz, L.; Valasinas A.; Frydman, B. *J. Org. Chem.* 1981, 46, 864-867.
(7) Yu, L.; Muthukumaran, K.; Sazanovich, I. V.; Kirmaier, C.; Hindin, E.; Diers, J. R.; Boyle, P. D.; Bocian, D. F.; Holten, D.; Lindsey, J. S. *Inorg. Chem.* 2003, 42, 6629-6647.
(8) Laha, J. K.; Dhanalekshmi, S.; Taniguchi, M.; Ambroise, A.; Lindsey, J. S. *Org. Process Res. Dev.* 2003, 7, 799-812.
(9) (a) Johnson, A. W.; Kay, I. T. J. *Chem. Soc.* 1965, 1620-1629. (b) Murakami, Y.; Matsuda, Y.; Kanaoka, Y. *Bull. Chem. Soc. Jpn.* 1971, 44, 409-415. (c) Bullock, E.; Grigg, R.; Johnson, A. W.; Wasley, J. W. F. *J. Chem. Soc.* 1963, 2326-2335. (d) Smith, K. M.; Minnetian, O. M. *J. Chem. Soc. Perkin.* 1 1986, 277-280.
(10) Johnson, A. W.; Kay, I. T. *J. Chem. Soc.* 1961, 2418-2423.
(11) Clezy, P. S.; Liepa, A. J. *Aust. J. Chem.* 1971, 24, 1027-1040
(12) Dolphin, D.; Johnson, A. W.; van den Broek, P. *J. Chem. Soc. C* 1966, 880-884.
(13) Siya, R.; Spicer, L. D. *Synth. Commun.* 1992, 22, 2673-81.
(14) Taniguchi, M.; Ra, D.; Mo, G.; Balasubramanian, T.; Lindsey, J. S. *J. Org. Chem.* 2001, 66, 7342-7354.
(15) Liu, H.-Y.; Lai, T.-S.; Yeung, L.-L.; Chang, C. K. *Org. Lett.* 2003, 5, 617-620.
(16) Paoloesse, R.; Froiio, A.; Mastroianni, M.; Russo, M.; Nurco, D. J.; Smith, K. M. *J. Porphyrins Phthalocyanines* 2003, 7, 585-592.
(17) Muthukumaran, K.; Ptaszek, M.; Noll, B.; Scheidt, W. R.; Lindsey, J. S. *J. Org. Chem.* 2004, 69, 5354-5364.
(18) Zaidi, S. H. H.; Muthukumaran, K.; Tamaru, S.-I.; Lindsey, J. S. *J. Org. Chem.* 2004, 69, 8356-8365.
(19) Yadav, J. S.; Reddy, B. V. S.; Shubashree, S.; Sadashiv, K. *Tetrahedron Lett.* 2004, 45, 2951-2954.
(20) Campiani, G.; Nacci, V.; Bechelli, S.; Clani, S. M.; Garofalo, A.; Fiorini, I.; Wikstrom, H.; de Boer, P.; Liao, Y.; Tepper, P. G.; Cagnotto, A.; Mennini, T. *J. Med. Chem.* 1998, 41, 3763-3772.
(21) Strachan, J.-P.; O'Shea, D. F.; Balasubramanian, T.; Lindsey, J. S. *J. Org. Chem.* 2000, 65, 3160-3172.
(22) Lindsey, J. S.; Woodford, J. N. *Inorg. Chem.* 1995, 34, 1063-1069.
(23) O'Shea, D. F.; Miller, M. A.; Matsueda, H.; Lindsey, J. S. *Inorg. Chem.* 1996, 35, 7325-7338.
(24) Lindsey, J. S. In *The Porphyrin Handbook*; Kadish, K. M., Smith, K. M., Guilard, R., Eds.; Academic Press: San Diego, Calif., 2000; Vol. 1, pp 45-118.
(25) Lindsey, J. S.; Schreiman, I. C.; Hsu, H. C.; Kearney, P. C.; Marguerettaz, A. M. *J. Org. Chem.* 1987, 52, 827-836.
(26) Rao, P. D.; Dhanalekshmi, S.; Littler, B. J.; Lindsey, J. S. *J. Org. Chem.* 2000, 65, 7323-7344.

The foregoing is illustrative of the present invention, and is not to be construed as limiting thereof. The invention is defined by the following claims, with equivalents of the claims to be included therein.

The invention claimed is:
1. A linear tetrapyrrole having a 19-acyl group and a 1-protecting group, wherein said protecting group is selected from the group consisting of halo, thio, acetate, sulfonate, and triflate.
2. The linear tetrapyrrole of claim 1, wherein said linear tetrapyrrole is selected from the group consisting of bilanes, bilins, bilenes, and biladienes.
3. The linear tetrapyrrole of claim 1, wherein said 19-acyl group is a substituent of the formula —C(O)R, where R is: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, acyloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, or a water soluble group.
4. The linear tetrapyrrole of claim 1 selected from the group consisting of compounds of Formula IIa, IIb, IIc, IId, IIe, and IIf:

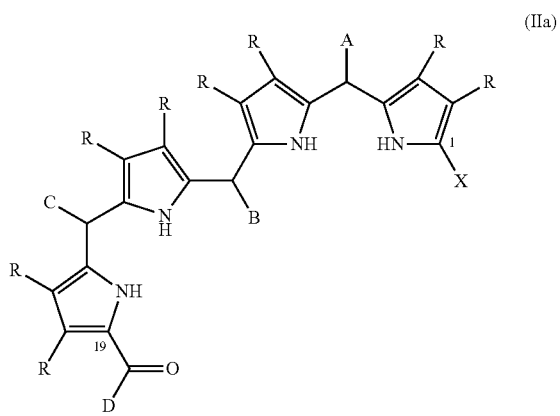

(IIa)

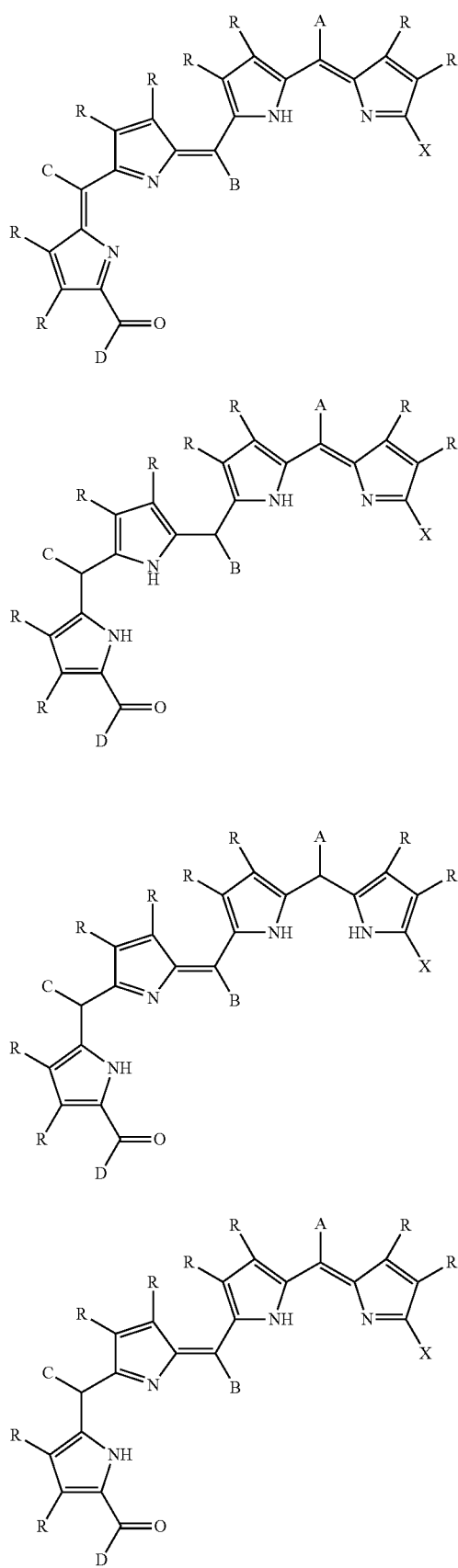
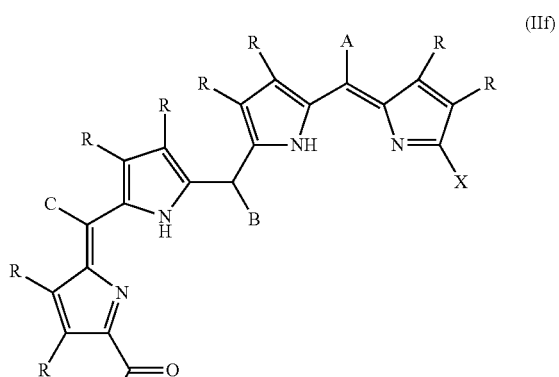

wherein:

X is a protecting group selected from the group consisting of halo, thio, acetate, sulfonate, and triflate;

A, B, C, and D are each independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups;

each R is independently selected from the group consisting of: H, alkyl, alkenyl, alkynyl, cycloalkyl, cycloalkylalkyl, cycloalkylalkenyl, cycloalkylalkynyl, heterocyclo, hetero cycl o alkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups;

or an adjacent pair of two R groups may together form an annulated arene or annulated alkene.

5. The linear tetrapyrrole of claim 4, wherein said compound has the structure of Formula IIa:

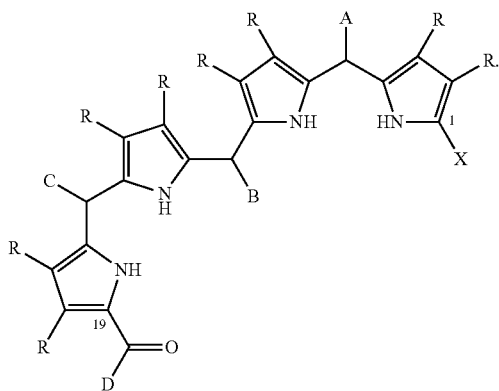

(IIa)

6. A method of making a compound of Formula IIa:

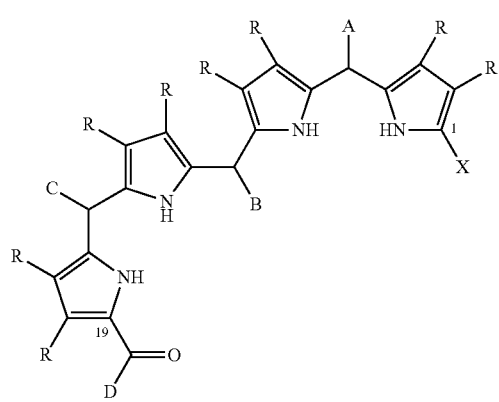

(IIa)

comprising reacting a compound of Formula III with a compound of Formula VII:

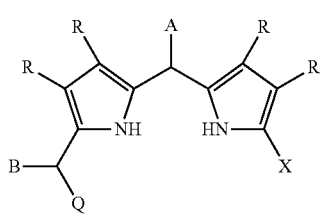

(III)

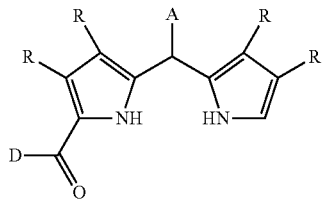

(VII)

in the presence of an acid catalyst to produce the compound of Formula IIa, wherein:

Q is a leaving group selected from the group consisting of acetate, trifluoroacetate, hydroxyl, sulfonate, triflate and mesylate;

X is a protecting group selected from the group consisting of halo, thio, acetate, sulfonate, and triflate;

A, B, C, and D are each independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups;

each R is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups;

or an adjacent pair of two R groups may together form an annulated arene or annulated alkene.

7. A complex of (i) a metal ion; (ii) a linear tetrapyrrole, and (iii) optionally at least one counterion;

wherein said linear tetrapyrrole has a 19-acyl group substituted thereon, and wherein said linear tetrapyrrole is at least partially unsaturated.

8. The complex of claim 7, wherein said linear tetrapyrrole is selected from the group consisting of bilins, bilenes, and biladienes.

9. The complex of claim 7, wherein said metal is magnesium, zinc, copper, palladium, nickel, or indium.

10. The complex of claim 7, wherein said linear tetrapyrrole is selected from the group consisting of compounds of Formula IIa, IIb, IIc, IId, IIe, and IIf:

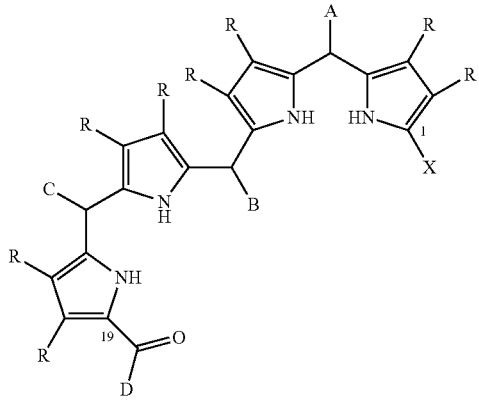
(IIa)

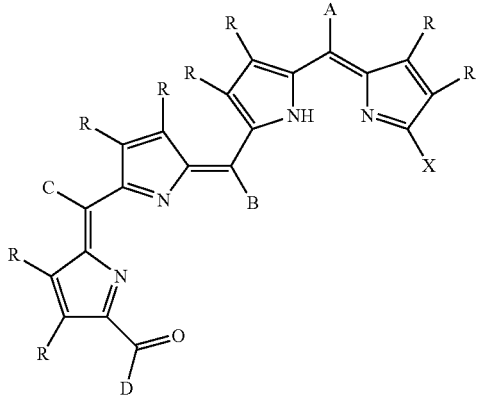
(IIb)

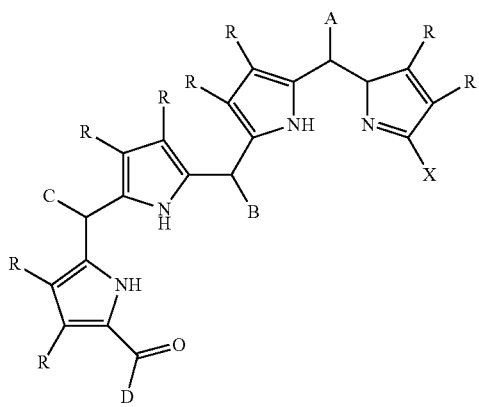
(IIc)

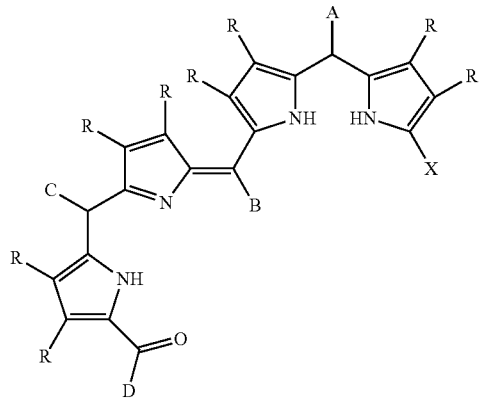
(IId)

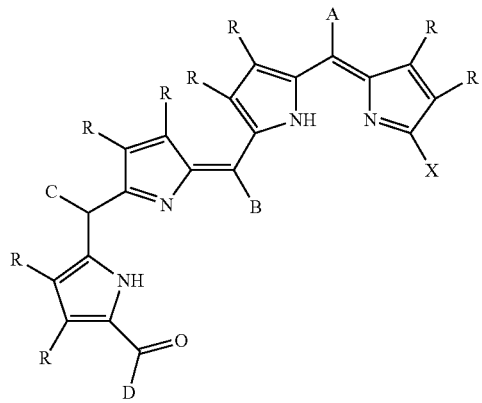
(IIe)

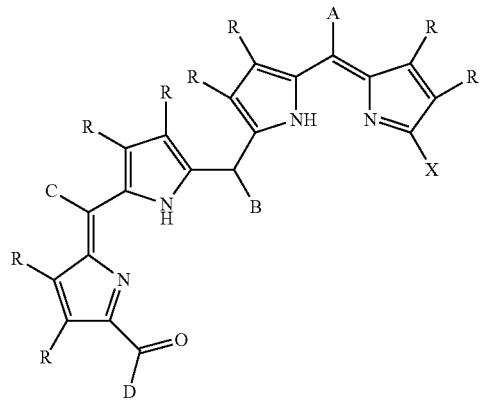
(IIf)

wherein:
X is a protecting group selected from the group consisting of halo, thio, acetate, sulfonate, and triflate;
A, B, C, and D are each independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups;

each R is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups;

or an adjacent pair of two R groups may together form an annulated arene or annulated alkene.

11. The complex of claim 10, wherein said linear tetrapyrrole has the structure of Formula IIa:

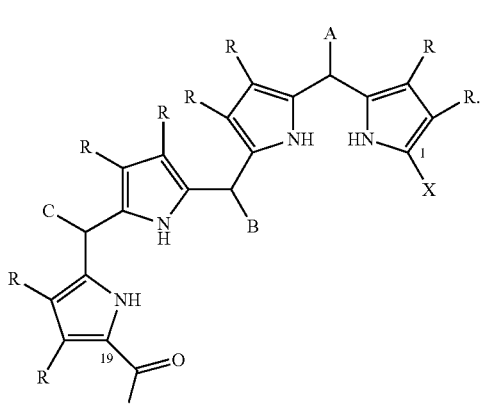
(IIa)

12. A complex of the formula DMR$^1$R$^2$, wherein: D is a linear tetrapyrrole having a 19-acyl group substituted thereon, M is boron, and R$^1$ and R$^2$ are each independently selected from the group consisting of alkyl, alkenyl, alkynyl, and aryl, each of which can be unsubstituted or substituted one or more times with a substituent selected from the group consisting of alkyl, alkenyl, alkynyl, aryl, alkoxy, alkylcarbonyl, alkylcarbonyloxy, alkylsulfinyl, alkylsulfonyl, alkylthio, halo, cyano, nitro, sulfo, oxo, formyl, azido, and carbamoyl.

13. The complex of claim 12 in solid form.

14. The complex of claim 12, wherein said linear tetrapyrrole is selected from the group consisting of compounds of Formula IIa, IIb, IIc, IId, IIe, and IIf:

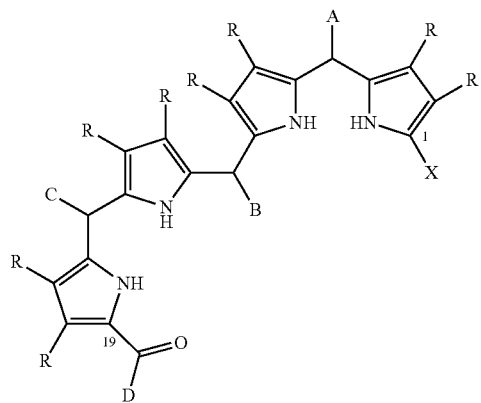
(IIa)

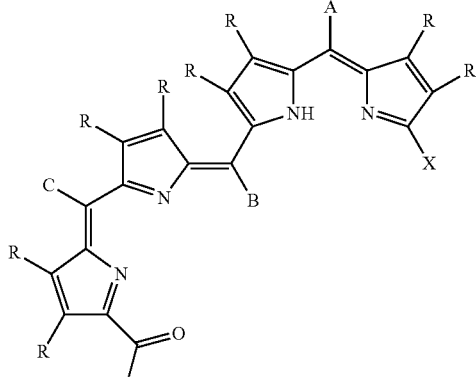
(IIb)

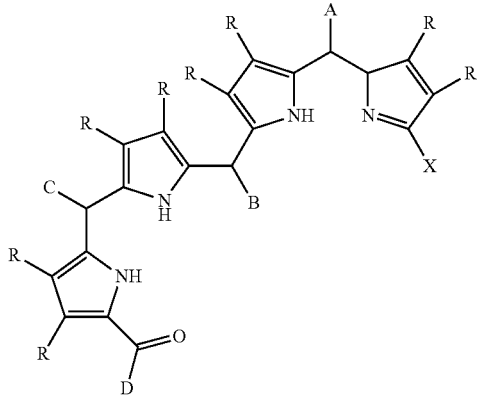
(IIc)

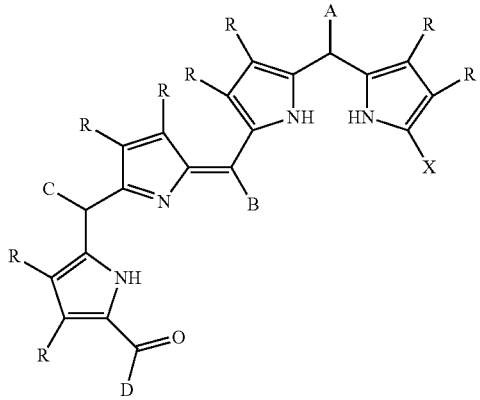
(IId)

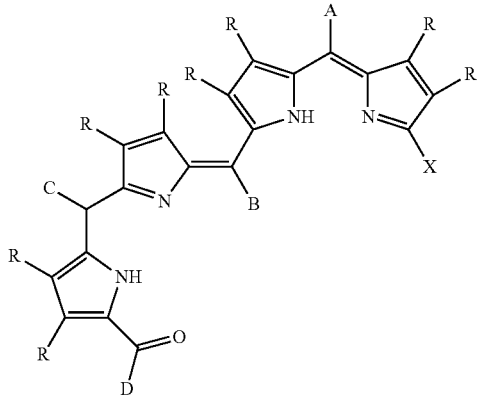
(IIe)

-continued

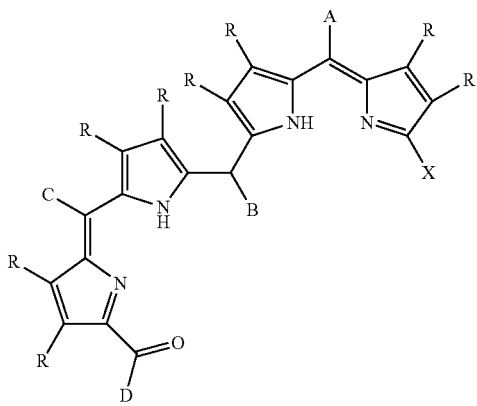

(IIf)

wherein:
X is a protecting group selected from the group consisting of halo, thio, acetate, sulfonate, and triflate;
A, B, C, and D are each independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups;
each R is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups;

or an adjacent pair of two R groups may together form an annulated arene or annulated alkene.

15. The complex of claim 14, wherein said linear tetrapyrrole has the structure of Formula IIa:

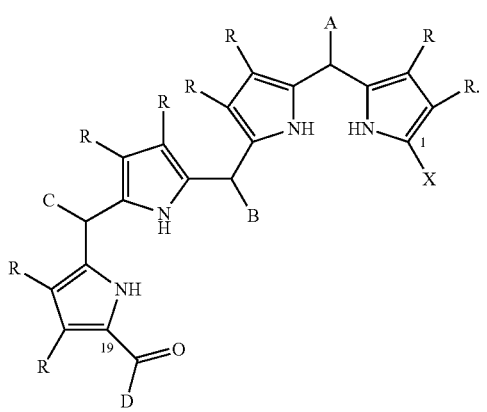

(IIa)

16. The linear tetrapyrrole of claim 1 having the structure:

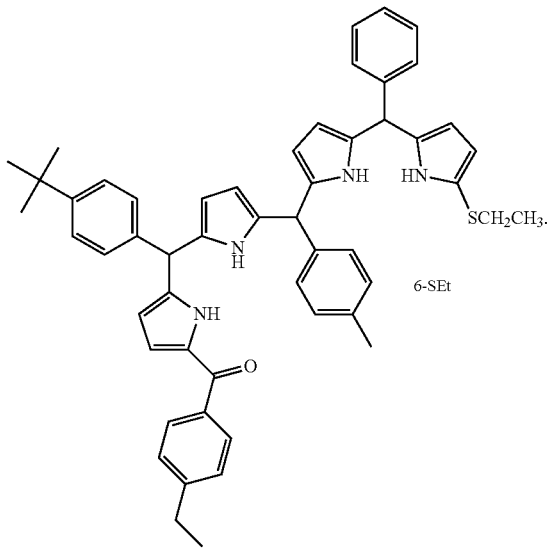

* * * * *

UNITED STATES PATENT AND TRADEMARK OFFICE
CERTIFICATE OF CORRECTION

PATENT NO. : 8,188,298 B2
APPLICATION NO. : 13/170492
DATED : May 29, 2012
INVENTOR(S) : Lindsey et al.

It is certified that error appears in the above-identified patent and that said Letters Patent is hereby corrected as shown below:

In the Specification:

Column 19, Scheme 2-Part 2 of 2:
    Please correct "On-flash ABCD-Metalloporphyrin Synthesis"
    to read -- On-flask ABCD Metalloporphyrin Synthesis --

Column 23, Scheme 4, Line 32: Please correct "NH$_4$SCN, I$_2$MeOH,"
    to read -- NH$_4$SCN, I$_2$, MeOH, --

Column 31, Please correct the figure 9-M below:

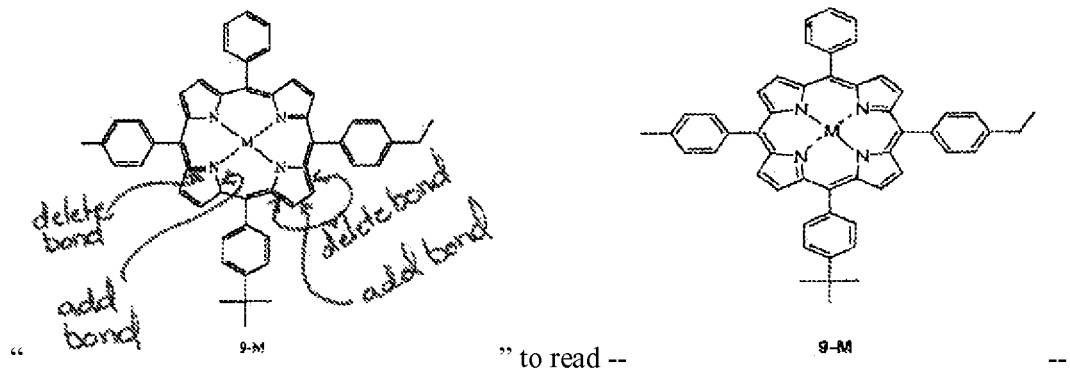

Column 38, Table 4, Line 52, Please correct: "6*" to read -- $6^b$ --

Column 38, Line 57: Please correct "in to luene," to read -- in toluene, --

In the Claims:

Column 52, Claim 3, Line 38: Please correct "acyloxy," to read -- aryloxy, --

Signed and Sealed this
Second Day of July, 2013

Teresa Stanek Rea
*Acting Director of the United States Patent and Trademark Office*

CERTIFICATE OF CORRECTION (continued)
U.S. Pat. No. 8,188,298 B2

Column 54, Claim 4, Line 51: Please correct "hetero cycl o alkyl,"
to read -- heterocycloalkyl, --

Column 56, Claim 6, Formula (VII): Please correct the formula below:

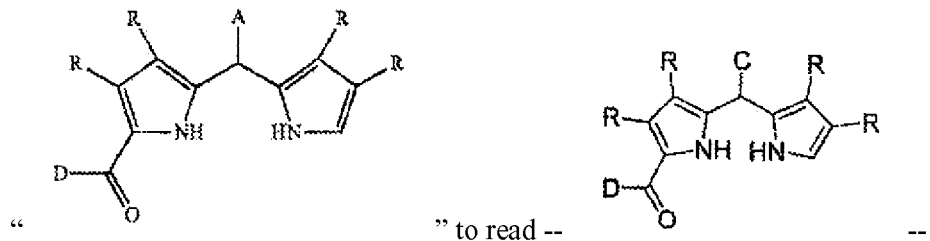

" to read -- --

Column 57, Claim 10, Figure (IIc): Please correct the formula below:

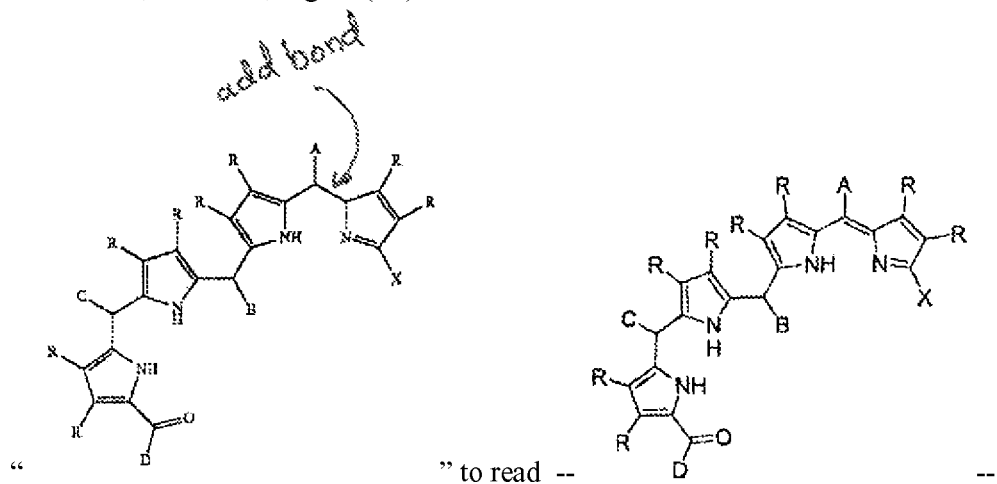

" to read -- --

Column 60, Claim 14, Figure (IIc): Please correct the formula below:

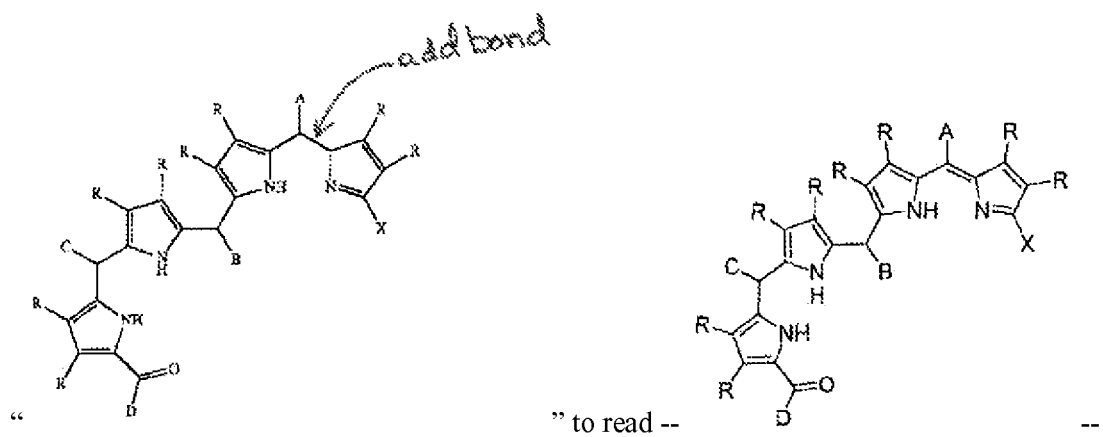

" to read -- --